United States Patent
Zahn et al.

(10) Patent No.: US 8,937,095 B2
(45) Date of Patent: Jan. 20, 2015

(54) ANTICANCER COMPOUNDS

(71) Applicants: Stephan Karl Zahn, Vienna (AT); Patrizia Sini, Brunn am Gebirge (AT); Bojan Bister, Biberach an der Riss (DE)

(72) Inventors: Stephan Karl Zahn, Vienna (AT); Patrizia Sini, Brunn am Gebirge (AT); Bojan Bister, Biberach an der Riss (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 13/937,437

(22) Filed: Jul. 9, 2013

(65) Prior Publication Data

US 2014/0018405 A1 Jan. 16, 2014

(30) Foreign Application Priority Data

Jul. 11, 2012 (EP) .................................... 12176037

(51) Int. Cl.
 *C07D 209/14* (2006.01)
 *C07D 209/34* (2006.01)
(52) U.S. Cl.
 CPC ............ *C07D 209/34* (2013.01); *C07D 209/14* (2013.01)
 USPC .......................................... 514/418; 548/486
(58) Field of Classification Search
 CPC ............................ C07D 209/14; C07D 209/34
 USPC .......................................... 548/486; 514/418
 See application file for complete search history.

(56) References Cited

U.S. PATENT DOCUMENTS

2011/0263565 A1  10/2011  Treu et al.
2012/0107304 A1  5/2012  Solca et al.

FOREIGN PATENT DOCUMENTS

WO  2010012747 A1  2/2010
WO  2011134898 A1  11/2011

OTHER PUBLICATIONS

International Search Report, Form PCT/ISA/210, and Written Opinion, Form PCT/ISA/237, for corresponding application PCT/EP2013/064402, date of mailing Aug. 22, 2013.

*Primary Examiner* — Shawquia Jackson
(74) *Attorney, Agent, or Firm* — Michael P. Morris; Alan R. Stempel

(57) ABSTRACT

The invention describes dual Aurora kinase/MEK inhibitors and their use in therapy.

5 Claims, No Drawings

ANTICANCER COMPOUNDS

The invention describes dual Aurora kinase/MEK inhibitors, pharmaceutical compositions or combinations comprising such inhibitors and, optionally, one or more other active substances, particularly for use in methods of treatment or prevention as described herein, especially of cancer diseases (particularly of those cancers described herein).

In one embodiment, the therapeutic and/or preventive methods of this invention comprise the step of identifying a patient being susceptible to anti-cancer treatment and/or prevention, said identifying comprising testing whether the patient is susceptible to MEK inhibitor treatment. In particular, said identifying comprising testing whether patient's cancer is responsive to MEK signalling pathway or whether MEK is activated in patient's cancer, particularly said identifying comprising testing whether in patient's cancer either RAF (e.g. BRAF) or RAS (e.g. KRAS and/or NRAS) is mutated.

Such therapeutic and/or preventive methods of this invention further comprise administering a dual Aurora kinase/MEK inhibitor, pharmaceutical composition or combination according to this invention to the patient determined as being susceptible to the treatment and/or prevention.

Further, the usability of a dual Aurora kinase/MEK inhibitor, a pharmaceutical composition or combination each as described herein for a therapeutic and/or preventive method or use according to this invention in a patient being susceptible to Aurora kinase and/or MEK inhibitor treatment, such as e.g. either in a patient whose cancer is responsive to MEK signalling pathway (or in whose cancer MEK is activated) or in a patient whose cancer is independent on the MEK signalling pathway (irrespective of the BRAF/RAS mutation status of the tumor), in particular in a patient whose cancer has a mutation in BRAF or RAS, e.g., such as defined herein, is contemplated.

Further, the dual Aurora kinase/MEK inhibitors, pharmaceutical compositions or combinations of the invention are also useful in the treatment of conditions in which the inhibition of MEK and/or Aurora kinase is beneficial.

Further, the present invention refers to a method for treating and/or preventing cancer types which are sensitive or responsive to MEK (e.g. MEK1 and/or MEK2) inhibition, e.g. such cancer types where the MAPK signaling pathway is hyperactivated, particularly such cancer types with RAS (e.g. KRAS and/or NRAS) or RAF (e.g. BRAF) mutation; and/or which are sensitive or responsive to Aurora (particularly Aurora-B) kinase inhibition, said method comprising administering a therapeutically effective amount of a dual Aurora kinase/MEK inhibitor of this invention (optionally in combination with one or more other anti-cancer agents) to the patient in need thereof.

A dual Aurora kinase/MEK inhibitor within the meaning of this invention refers to a compound which is both an inhibitor of one or more Aurora kinases (particularly of Aurora-B) and an inhibitor of one or more MEK kinases (MEK1 and/or MEK2). For the avoidance of any doubt, a dual Aurora kinase/MEK inhibitor within the meaning of this invention refers to one compound having said two different properties, namely that of an Aurora kinase inhibitor (AKI) and that of a MEK inhibitor.

Aurora kinases (Aurora-A, Aurora-B, Aurora-C) are serine/threonine protein kinases that are essential for proliferating cells and have been identified as key regulators of different steps in mitosis and meiosis, ranging from the formation of the mitotic spindle to cytokinesis. Aurora family kinases are critical for cell division, and have beeen closely linked to tumorigenesis and cancer susceptibility. In various human cancers over-expression and/or up-regulation of kinase activity of Aurora-A, Aurora-B and/or Aurora C has been observed. Over-expression of Aurora kinases correlates clinically with cancer progression and poor survival prognosis. Aurora kinases are involved in phosphorylation events (e.g. phosphorylation of histone H3) that regulate the cell cycle. Misregulation of the cell cycle can lead to cellular proliferation and other abnormalities.

The serine/threonine kinase Aurora-B is involved in the regulation of several mitotic processes, including chromosome condensation, congression and segregation as well as cytokinesis. Inactivation of Aurora B abrogates the spindle assembly checkpoint (SAC) and causes premature mitotic exit without cytokinesis, resulting in polyploid cells that eventually stop further DNA replication. Aurora B inhibitors induce a mitotic override (mitotic slippage). Inhibitors of Aurora B kinase also block proliferation in various human cancer cell lines and induce polyploidy, senescence and apoptosis.

Aurora B inhibitors abrogate the spindle assembly checkpoint (SAC) and induce a mitotic override (mitotic slippage), yielding aberrant polyploid cells rather then a cell cycle arrest. Polyploid cells spend little time in mitosis as check point controls are overridden and become genetically unstable. Inhibition of Aurora B kinase can predominantly induce slow senescence-associated cell death rather than apoptosis which may distinguish it from other anti-mitotic principles. In common with other M-phase targeting drugs is the general applicablility of this anti-cancer treatment principle. Aurora kinases are indeed restrictedly expressed during mitosis and thus exclusively found in proliferating cells.

MEK (mitogen-activated protein kinase/extracellular signal related kinase kinase) is a key player in the "RAS-RAF-MEK-ERK pathway" which has pathophysiological relevance in various cancer types. The direct downstream substrate of MEK is ERK which in its phosphorylated state enters the cell nucleus and is involved in the regulation of gene expression. MEK is frequently activated in tumors, especially when either RAS or BRAF is mutated. BRAF and RAS mutations are known to be mutually exclusive. According to the literature, RAF-inhibitors are not active in KRAS mutated cancers, whereas MEK inhibitors could principally work in both KRAS and BRAF mutated cancers (see also Table 1 below). No difference in relevance and function between the two MEK isoforms (MEK1, MEK2) is known to date. The RAS-dependent RAF/MEK/ERK1/2 mitogen activated protein (MAP) kinase signaling pathway plays an important role in the regulation of cell proliferation and survival.

Constitutive activation of the RAS/RAF/MEK/ERK signaling pathway is involved in malignant transformation. Mutational activation of KRAS (approximately 15% of all cancers) and BRAF (about 7% of all cancers) are common mutually exclusive events found in a variety of human tumors (see Table 1 below).

TABLE 1

Occurrence of BRAF and RAS mutations in various cancers

| KRAS mutation: | BRAF mutation: | NRAS mutation: |
|---|---|---|
| ~70% Pancreas | ~46% Thyroid | ~20% Melanoma |
| ~37% CRC | ~43% Melanoma | |
| ~18% NSCLC | ~12% Ovarian | |
| ~14% Ovarian | ~11% CRC | |
| ~8% Prostate | ~7% Prostate | |
| ~5% Breast | <5% NSCLC | |
| ~4% HCC | | |

CRC: Colorectal cancer
NSCLC: Non-small cell lung cancer
HCC: Hepatocellular cancer Taken together, a dual Aurora kinase/MEK inhibitor of this invention—as an inhibitor of Aurora B kinase, a target essential for mitosis of all cancer cells independent of oncogenic mutations—shows efficacy in a broad range of cancers by inducing polyploidy and senescence. In addition, due to potent inhibition of MEK signaling, a dual Aurora kinase/MEK inhibitor of this invention is particularly effective in a subset of cancers dependent on oncogenic MEK signaling due to mutations in RAS or RAF genes.

Accordingly, a dual Aurora kinase/MEK inhibitor of this invention is useful for treating and/or preventing
a) such cancer types which are sensitive to or responsive to MEK (e.g. MEK1 and/or MEK2) inhibition, particularly such cancer types where the MAPK signaling pathway is hyperactivated e.g. due to RAS or RAF mutation; and/or
b) such cancer types which are sensitive to or responsive to Aurora (particularly Aurora-B) kinase inhibition, e.g. such cancer types which are sensitive to or responsive to induction of mitotic checkpoint override, cancer cell polyploidy and/or (slow senescence-associated) cancer cell death.

Hence, for example, cancer types amenable for the therapy according to this invention include, without being limited to, colorectal cancer (colorectal carcinoma, CRC) especially with KRAS mutated tumors or KRAS wildtype tumors, pancreatic cancer (pancreatic adenocarcinoma, PAC) especially with KRAS mutated or KRAS wildtype tumors, melanoma especially with BRAF mutation or of BRAF wildtype, and/or non-small-cell lung cancer (non-small-cell lung carcinoma, NSCLC) especially with KRAS mutation.

In a particular embodiment of this invention, a dual Aurora kinase/MEK inhibitor according to this invention is both an inhibitor of Aurora kinase B and an inhibitor of the kinases MEK1 and/or MEK2.

Examples of dual Aurora kinase/MEK inhibitors according to this invention can be found in WO 2010/012747, the disclosure of which is incorporated herein by reference in its entirety.

For example, a dual Aurora kinase/MEK inhibitors according to this invention is of general formula (1)

(1)

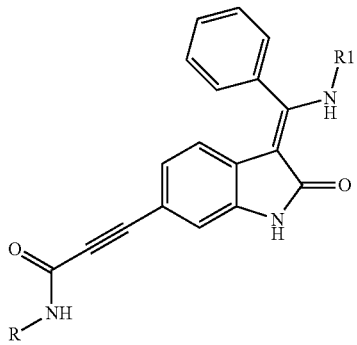

wherein
R1 is 4-(4-methylpiperazin-1-yl)-phenyl, 4-(mono- or dimethylaminomethyl)-phenyl, or 4-(pyrrolidin-1-ylmethyl)-phenyl,
R is $C_{1-6}$alkyl (such as e.g. ethyl, isopropyl, sec-butyl, (2R)-butan-2-yl or 3-pentyl), mono- or di-fluoro substituted $C_{1-6}$alkyl (such as e.g. 2,2-difluoroethyl or 2-fluoroethyl), mono-hydroxy substituted $C_{1-6}$alkyl (such as e.g. 2-hydroxyethyl or (2S)-1-hydroxypropan-2-yl), $C_{3-7}$cycloalkyl (such as e.g. cyclobutyl, cyclopropyl or cyclopentyl), phenyl, or mono- or di-halo substituted phenyl (such as e.g. 2-fluorophenyl, 3-fluorophenyl, 2-chlorophenyl or 3-chlorophenyl), optionally in the form of the prodrugs, the tautomers, the racemates, the enantiomers, the diastereomers and the mixtures thereof, and optionally the N-oxides or pharmacologically acceptable acid addition salts thereof.

Preferably, a dual Aurora kinase/MEK inhibitor according to this invention is selected from the group A consisting of the following compounds 1 to 27, optionally in the form of the tautomers or pharmaceutically acceptable salts thereof:

1) N-ethyl-3-[3-[[4-(4-methylpiperazin-1-yl)anilino]-phenylmethylidene]-2-oxo-1H-indol-6-yl]prop-2-ynamide

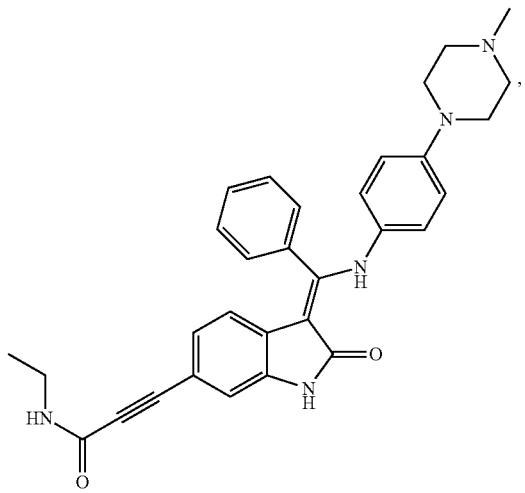 [SMILES: CCNC(=O)C#Cc1ccc2c(c1)NC(=O)/C2=C(\Nc1ccc(N2CCN(C)CC2)cc1)c1ccccc1]

2) N-(2,2-difluoroethyl)-3-[3-[[4-(dimethylaminomethyl)anilino]-phenylmethylidene]-2-oxo-1H-indol-6-yl]prop-2-ynamide

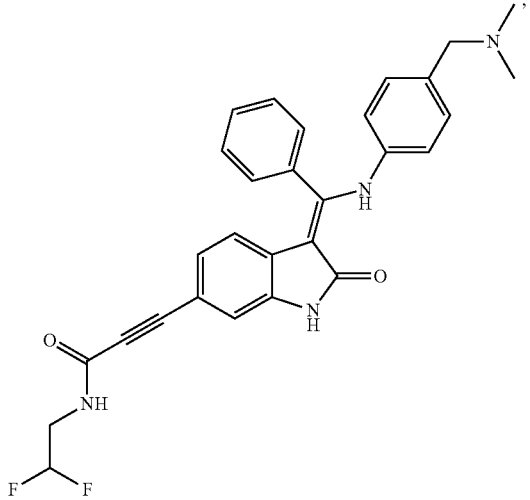 [SMILES: CN(C)Cc1ccc(N/C(=C2\C(=O)Nc3cc(C#CC(=O)NCC(F)F)ccc32)c2ccccc2)cc1]

3) N-(2,2-difluoroethyl)-3-[2-oxo-3-[phenyl-[4-(pyrrolidin-1-ylmethyl)anilino]methylidene]-1H-indol-6-yl]prop-2-ynamide
5) N-ethyl-3-[2-oxo-3-[phenyl-[4-(pyrrolidin-1-ylmethyl)anilino]methylidene]-1H-indol-6-yl]prop-2-ynamide
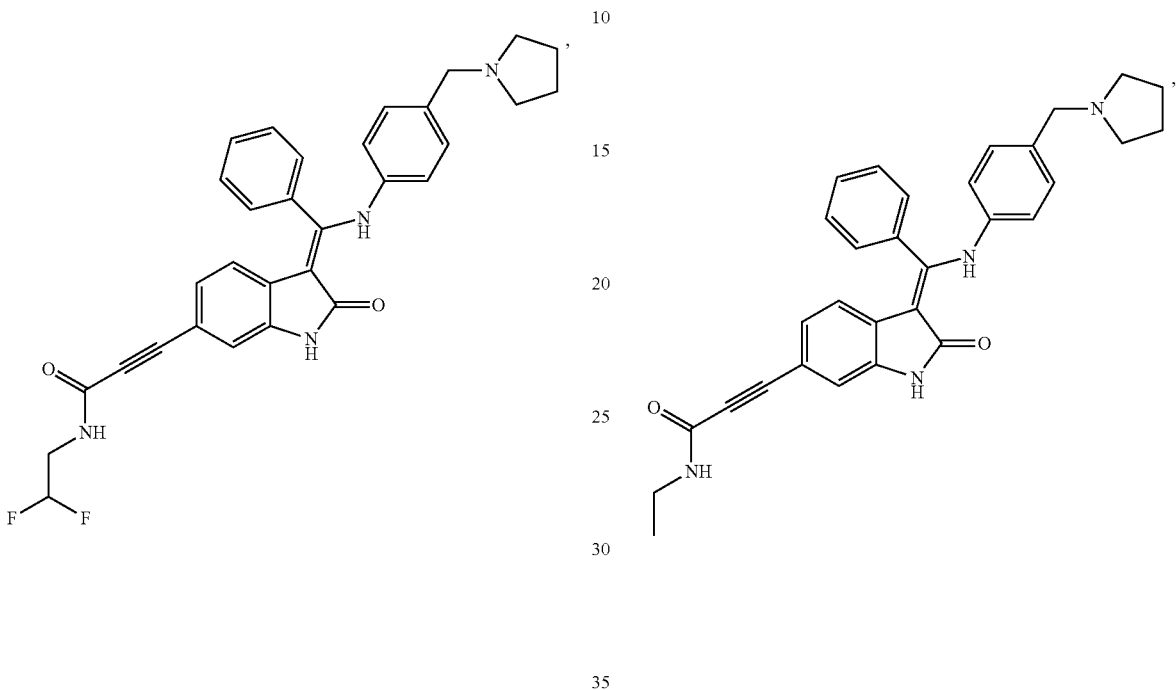
4) N-(2-fluoroethyl)-3-[2-oxo-3-[phenyl-[4-(pyrrolidin-1-ylmethyl)anilino]methylidene]-1H-indol-6-yl]prop-2-ynamide
6) 3-[3-[[4-(dimethylaminomethyl)anilino]-phenylmethylidene]-2-oxo-1H-indol-6-yl]-N-ethylprop-2-ynamide
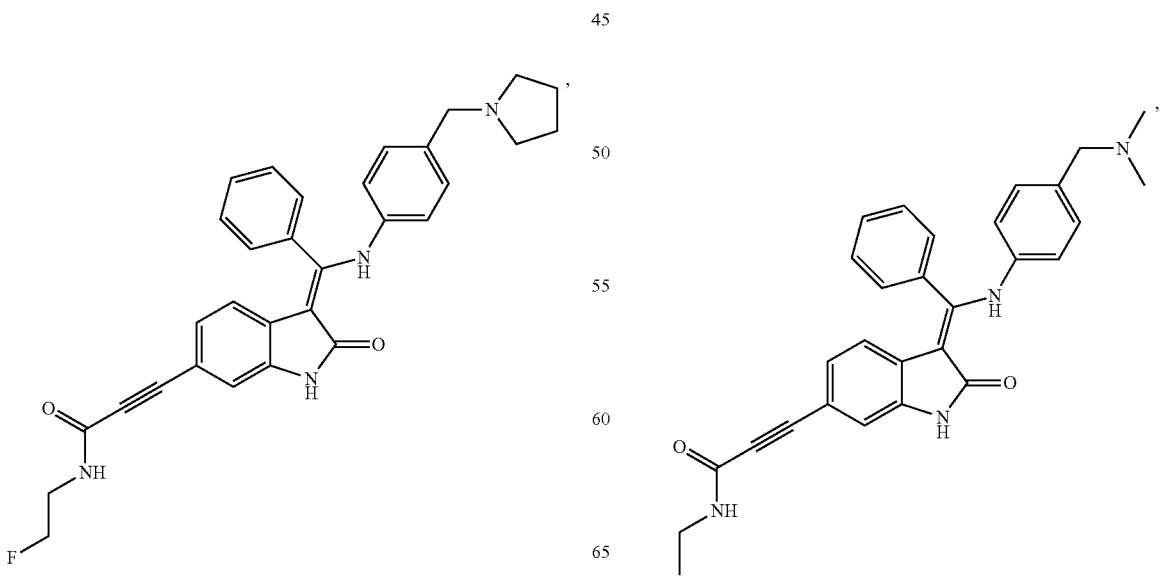

7) N-cyclobutyl-3-[3-[[4-(4-methylpiperazin-1-yl)anilino]-phenylmethylidene]-2-oxo-1H-indol-6-yl]prop-2-ynamide 9) 3-[3-[[4-(dimethylaminomethyl)anilino]-phenylmethylidene]-2-oxo-1H-indol-6-yl]-N-phenylprop-2-ynamide

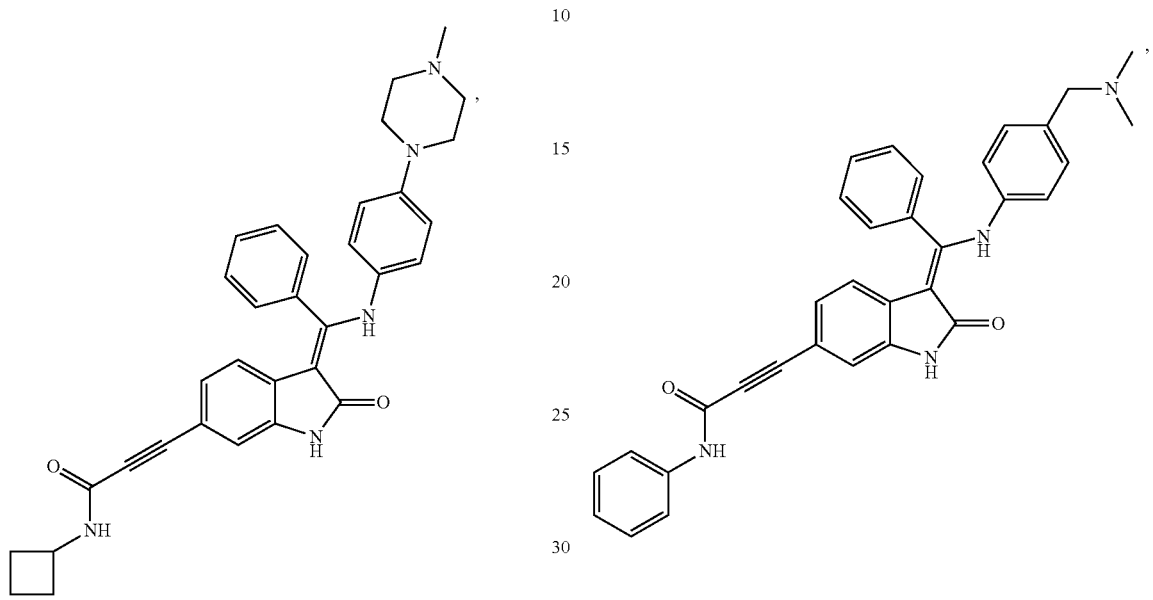

8) N-cyclopropyl-3-[3-[[4-(dimethylaminomethyl)anilino]-phenylmethylidene]-2-oxo-1H-indol-6-yl]prop-2-ynamide 10) N-cyclopentyl-3-[3-[[4-(dimethylaminomethyl)anilino]-phenylmethylidene]-2-oxo-1H-indol-6-yl]prop-2-ynamide

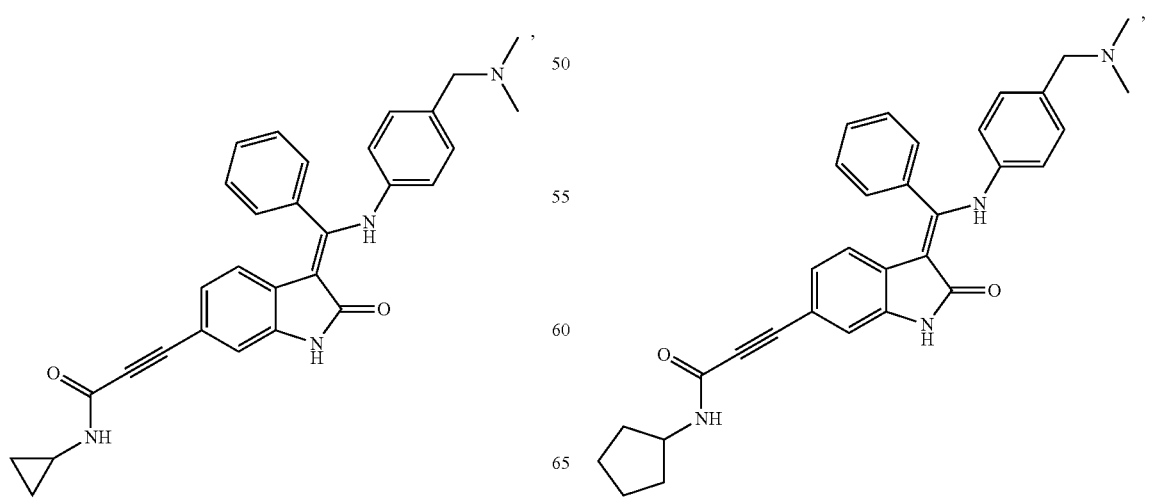

11) N-cyclopentyl-3-[3-[[4-(4-methylpiperazin-1-yl)anilino]-phenylmethylidene]-2-oxo-1H-indol-6-yl]prop-2-ynamide 13) 3-[3-[[4-(dimethylaminomethyl)anilino]-phenyl-methylidene]-2-oxo-1H-indol-6-yl]-N-(2-hydroxy-ethyl)prop-2-ynamide

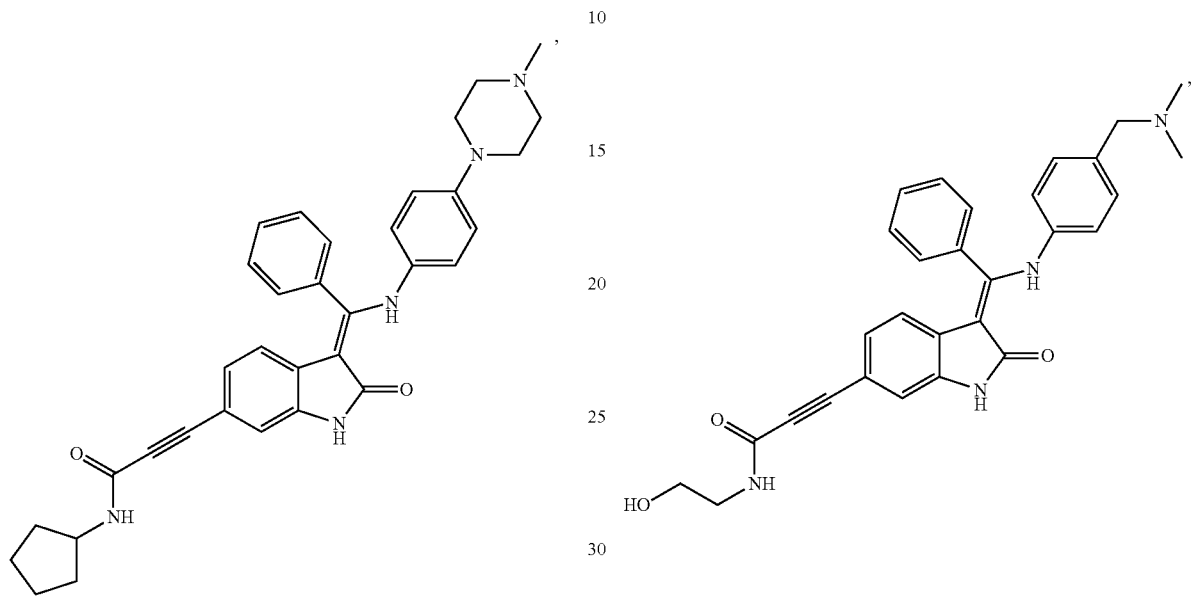

12) N-cyclobutyl-3-[3-[[4-(dimethylaminomethyl)anilino]-phenylmethylidene]-2-oxo-1H-indol-6-yl]prop-2-ynamide 14) 3-[3-[[4-(dimethylaminomethyl)anilino]-phenyl-methylidene]-2-oxo-1H-indol-6-yl]-N-propan-2-ylprop-2-ynamide

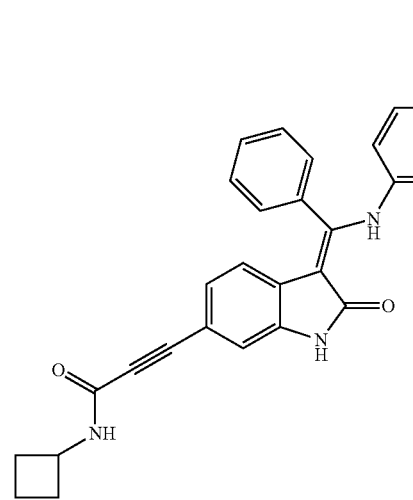

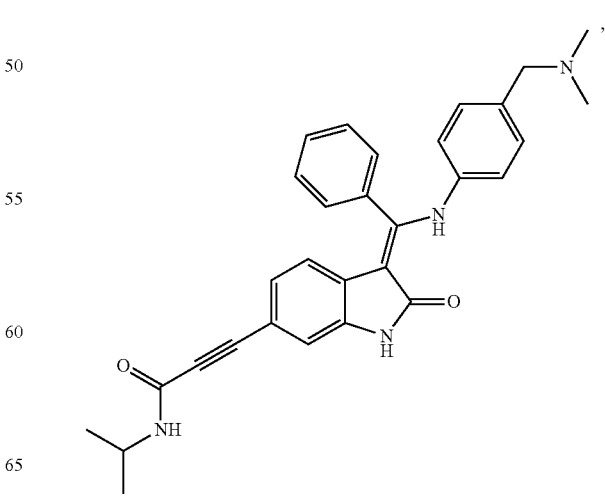

| 11 | 12 |
|---|---|
| 15) 3-[2-oxo-3-[phenyl-[4-(pyrrolidin-1-ylmethyl)anilino]methylidene]-1H-indol-6-yl]-N-propan-2-ylprop-2-ynamide | 17) N-(2-fluorophenyl)-3-[2-oxo-3-[phenyl-[4-(pyrrolidin-1-ylmethyl)anilino]methylidene]-1H-indol-6-yl]prop-2-ynamide |
| 16) N-(2-hydroxyethyl)-3-[2-oxo-3-[phenyl-[4-(pyrrolidin-1-ylmethyl)anilino]methylidene]-1H-indol-6-yl]prop-2-ynamide | 18) 3-[3-[[4-(dimethylaminomethyl)anilino]-phenyl-methylidene]-2-oxo-1H-indol-6-yl]-N-[(2S)-1-hydroxypropan-2-yl]prop-2-ynamide |

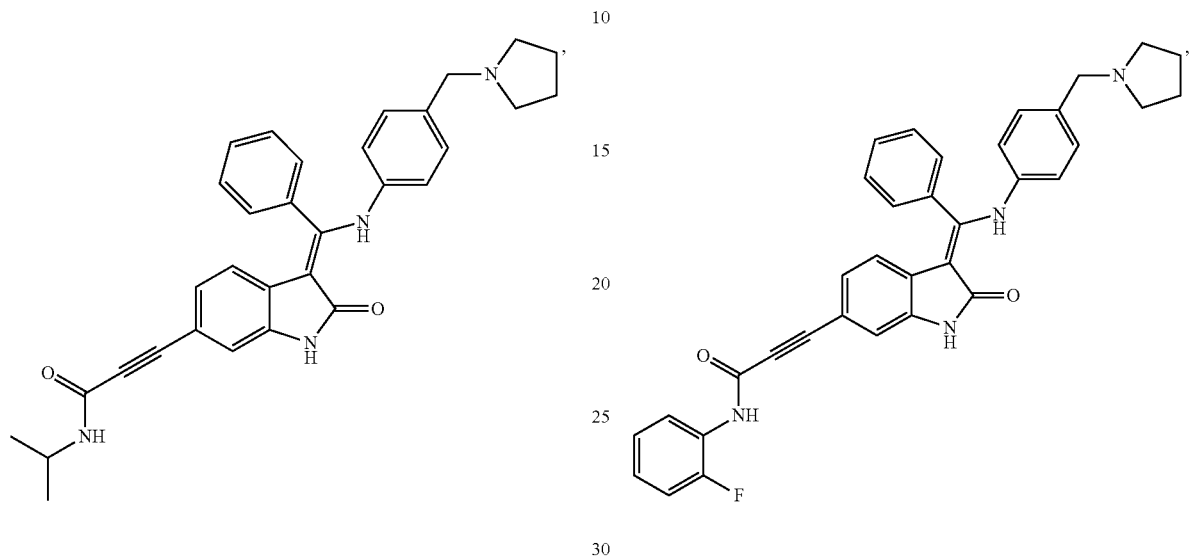

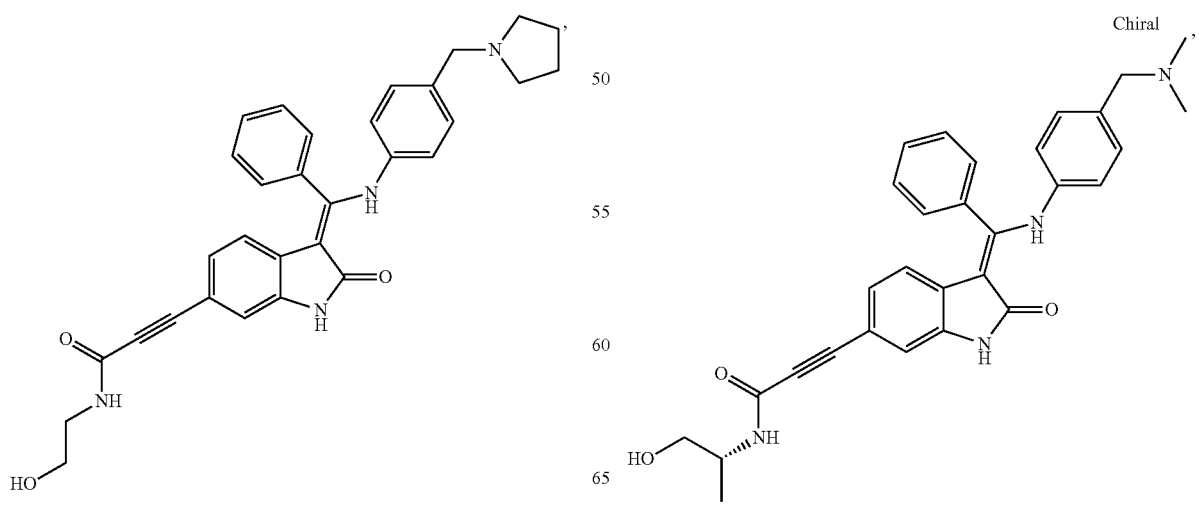

19) N-[(2S)-1-hydroxypropan-2-yl]-3-[2-oxo-3-[phenyl-[4-(pyrrolidin-1-ylmethyl)anilino]methylidene]-1H-indol-6-yl]prop-2-ynamide

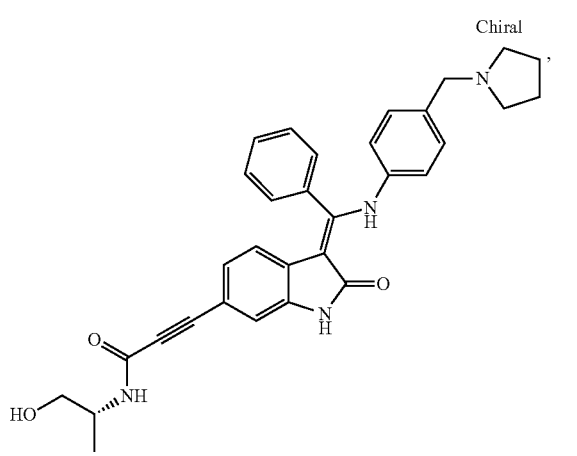 [SMILES: C[C@H](CO)NC(=O)C#Cc1ccc2c(c1)NC(=O)/C2=C(\Nc1ccc(CN2CCCC2)cc1)c1ccccc1]

20) N-[(2R)-butan-2-yl]-3-[2-oxo-3-[phenyl-[4-(pyrrolidin-1-ylmethyl)anilino]methylidene]-1H-indol-6-yl]prop-2-ynamide

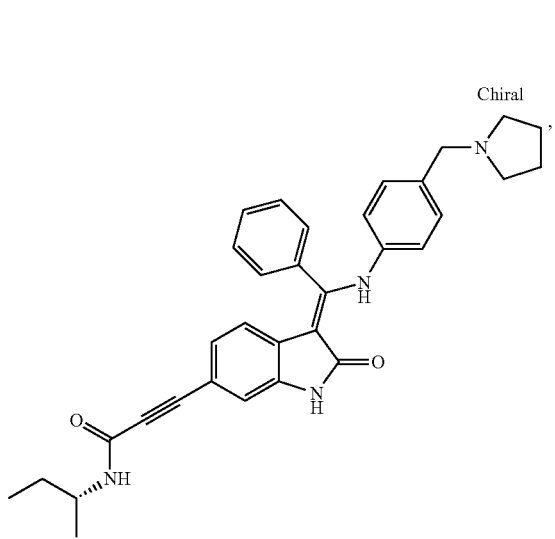 [SMILES: CC[C@@H](C)NC(=O)C#Cc1ccc2c(c1)NC(=O)/C2=C(\Nc1ccc(CN2CCCC2)cc1)c1ccccc1]

21) N-(3-chlorophenyl)-3-[2-oxo-3-[phenyl-[4-(pyrrolidin-1-ylmethy)anilino]methylidene]-1H-indol-6-yl]prop-2-ynamide

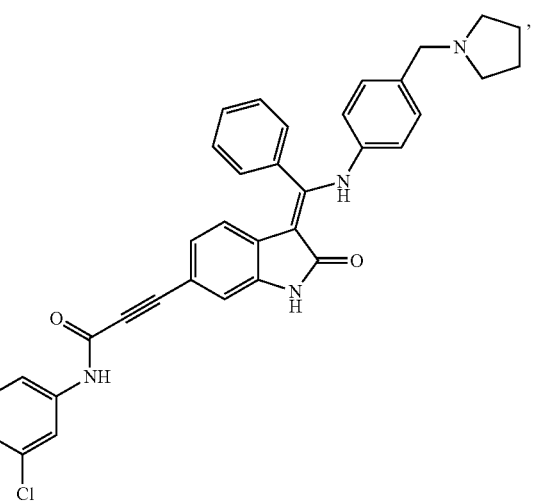

22) N-(3-chlorophenyl)-3-[3-[[4-(dimethylaminomethyl)anilino]-phenylmethylidene]-2-oxo-1H-indol-6-yl]prop-2-ynamide

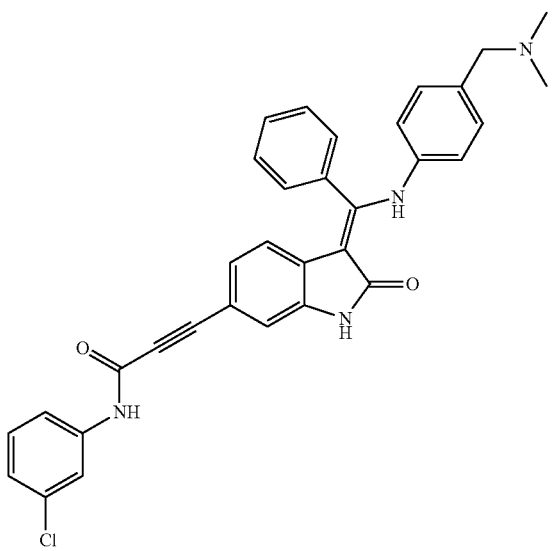 [SMILES: CN(C)Cc1ccc(N/C(=C2\C(=O)Nc3cc(C#CC(=O)Nc4cccc(Cl)c4)ccc32)c2ccccc2)cc1]

23) 3-[2-oxo-3-[phenyl-[4-(pyrrolidin-1-ylmethyl)anilino]methylidene]-1H-indol-6-yl]-N-phenylprop-2-ynamide
25) N-(3-fluorophenyl)-3-[2-oxo-3-[phenyl-[4-(pyrrolidin-1-ylmethyl)anilino]methylidene]-1H-indol-6-yl]prop-2-ynamide
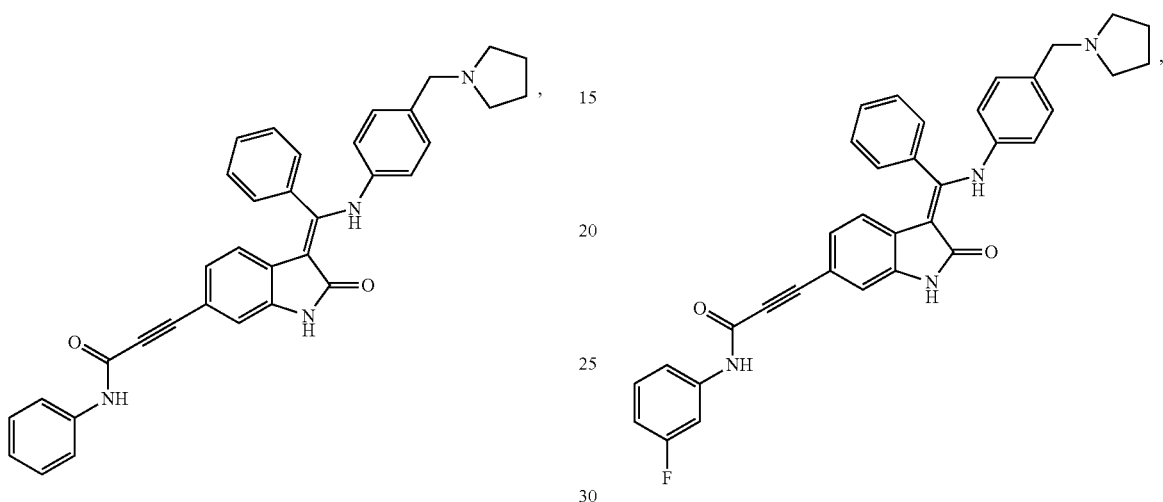
24) 3-[2-oxo-3-[phenyl-[4-(pyrrolidin-1-ylmethyl)anilino]methylidene]-1H-indol-6-yl]-N-pentan-3-ylprop-2-ynamide
26) 3-[3-[[4-(methylaminomethyl)anilino]-phenylmethylidene]-2-oxo-1H-indol-6-yl]-N-ethylprop-2-ynamide
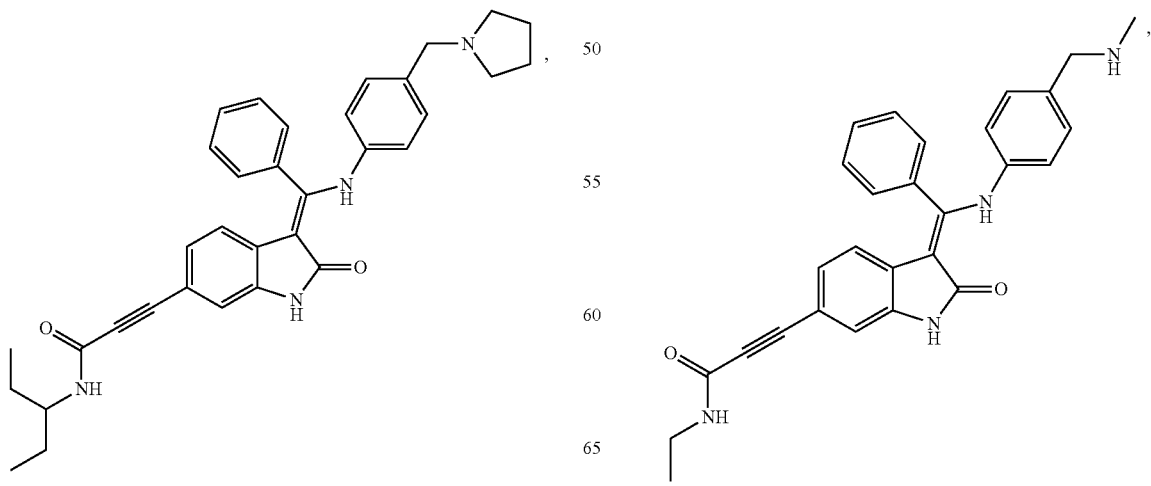

and 27) 3-[3-[[4-(dimethyloxidoaminomethyl)anilino]-phenylmethylidene]-2-oxo-1H-indol-6-yl]-N-ethyl-prop-2-ynamide

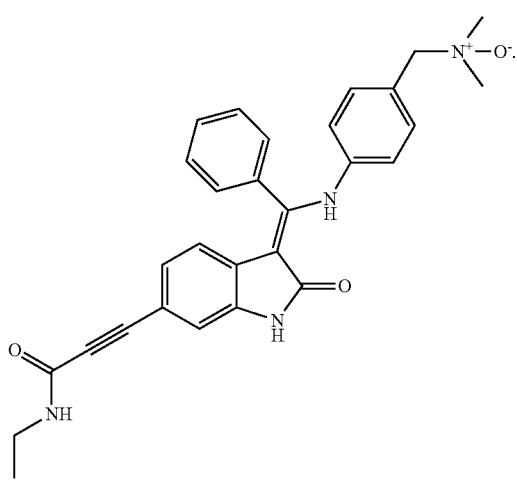

The dual inhibitory activity of the AKI/MEK inhibitors according to this invention can be determined according to methods customary to the skilled person, e.g. by methods known in the literature or as described herein or analogously thereto. Assays for measuring the Aurora kinase inhibitory activity as well as assays for measuring the MEK inhibitory activity of a compound are known from literature, are commercially available or are described herein in the examples section.

As stated herein, a dual Aurora kinase/MEK inhibitor in the scope of the present invention relates to a compound that exhibits inhibitory activity both on an Aurora kinase and on a kinase of MEK. Such inhibitory activity can be characterised each by the IC50 value. A dual Aurora kinase/MEK inhibitor of this invention has preferably an IC50 value for inhibition of an Aurora kinase (particularly Aurora B kinase) below 200 nM, preferably below 40 nM, more preferably below 10 nM (e.g. from about 1 nM to about 10 nM), preferably measured in the assay given in the following examples.

A dual Aurora kinase/MEK inhibitor of this invention has preferably an IC50 value for inhibition of a MEK kinase (MEK1 and/or MEK2) below 1000 nM, preferably below 200 nM, more preferably below 100 nM, even more preferably below 50 nM (e.g. below 30 nM), preferably measured in the assay given in the following examples.

A dual Aurora kinase/MEK inhibitor of this invention may have, for example, an IC50 value for inhibition of Aurora B kinase below 200 nM, preferably below 40 nM, more preferably below 10 nM (e.g. from about 1 nM to about 10 nM), and an IC50 value for inhibition of a MEK kinase (MEK1 and/or MEK2) below 1000 nM, preferably below 200 nM, more preferably below 100 nM, even more preferably below 50 nM (e.g. from about 1 nM to about 50 nM, such as e.g. MEK1 IC50 from about 1 nM to about 25 nM), preferably measured in the assays given in the following examples.

For illustrative example, the dual Aurora kinase/MEK inhibitors 1 to 6 of group A indicated above have IC50 values for inhibition of Aurora kinase B from about 2 nM to about 7 nM and IC50 values for inhibition of MEK1 from about 3 nM to about 25 nM (see table as follows), measured in the assays given in the examples section:

| Compound No. | Aurora B IC50 [nM] | MEK 1 IC50 [nM] |
|---|---|---|
| 1 | 2 | 10 |
| 2 | 7 | 6 |
| 3 | 4 | 3 |
| 4 | 5 | 6 |
| 5 | 5 | 5 |
| 6 | 3 | 25 |

This dual activity can also be confirmed in respective biomarker assays, such as e.g. in a phospho-histone H3 assay (e.g. H460, Cellomics), where p-histone H3 as marker for Aurora B kinase inhibition is inhibited, and in a phospho-ERK assay (e.g. SK-MEL 28, FACE ELISA), where p-ERK as marker for MEK inhibition is inhibited.

For example, a dual Aurora kinase/MEK inhibitor of this invention may have an EC50 value for reduction of phospho-histone H3 below 1000 nM, preferably below 200 nM, more preferably below 100 nM (e.g. from about 10 nM to about 50 nM), and an EC50 value for reduction of phospho-ERK below 1000 nM, preferably below 200 nM, more preferably below 100 nM (e.g. from about 30 nM to about 70 nM), preferably measured in the assays given in the following examples.

A certain exemplary dual Aurora kinase/MEK inhibitor of group A of this invention has IC50 value for inhibition of Aurora kinase B of 3 nM and IC50 values for inhibition of MEK1 and MEK2 of 25 nM and 4 nM, respectively, and has EC50 for reduction of phospho-histone H3 of 44 nM (synchronized H460 NSCLC cells, 1 h treatment, molecular phosphorylation assay, Cellomics) and EC50 for reduction of phospho-ERK of 59 nM (SK-MEL 28 melanoma cells, FACE ELISA), measured in the assays given in the examples section.

Direct inhibition of the MAP-kinase signaling pathway by the dual Aurora kinase/MEK inhibitors of this invention can be further confirmed in A375 and BRO melanoma cells.

The inhibitory activity on Aurora B kinase can be further confirmed by polyploidy phenotype. A certain exemplary dual Aurora kinase/MEK inhibitor of group A of this invention induces polyploidy in H460 cells as determined by DNA content analyses (Cellomics ArrayScan) over a wide range of concentrations. At 7 nM, 81% of the cells are polyploid after a 42 h exposure to the compound.

The cellular potency can be determined in various assays including Alamar Blue based proliferation assays performed in the presence of 10% fetal calf serum. For example, a dual Aurora kinase/MEK inhibitor of this invention may have an EC50 value in cell based proliferation assay below 1000 nM, preferably below 200 nM, more preferably below 100 nM, even more preferably below 50 nM (e.g. from about 5 nM to about 20 nM). A certain exemplary dual Aurora kinase/MEK inhibitor of group A of this invention inhibits the proliferation of 5 tumour cell lines tested (see table as follows):

| Cell line | Origin | $EC_{50}$ [nM] |
|---|---|---|
| NCI-H460 | NSCLC | 8 |
| A549 | NSCLC | 7 |
| HCT 116 | Colorectal carcinoma | 10 |
| A375 | Melanoma | 5 |
| PC-3 | Prostate carcinoma | 6 |

Many of the cell lines which are sensitive to a dual Aurora kinase/MEK inhibitor of this invention are mutated either in the RAS or the RAF genes.

The dual pathway inhibition of the compounds of this invention makes them particularly valuable for the use in the treatment and/or prevention of such conditions in which the dual pathway inhibition of MEK and Aurora kinase is beneficial.

For example, this dual pathway inhibition is expected to be beneficial for anti-cancer therapy in a variety of indications, including those with evidence for RAS (e.g. KRAS and/or NRAS) and/or BRAF mutational deregulation.

Thus, in one embodiment, the present invention refers to the use of the dual Aurora kinase/MEK inhibitors of this invention in the treatment of cancer or tumor having one or more of those mutations as indicated herein.

In another embodiment, the present invention refers to the use of the dual Aurora kinase/MEK inhibitors of this invention in the treatment of subsets of cancer with sensivity to or dependence on MEK-signalling pathway, particularly such subsets of cancer with one or more mutations in the BRAF or RAS (e.g. KRAS and/or NRAS) gene.

In another embodiment, the present invention refers to the use of the dual Aurora kinase/MEK inhibitors of this invention in the treatment of subsets of cancer which are independent from the MEK-signalling pathway (irrespective of the BRAF or RAS mutation status of the cancers).

In another embodiment, the present invention refers to the use of the dual Aurora kinase/MEK inhibitors of this invention in the treatment of subsets of cancer which are insensitive to the treatment with a selective MEK (MEK1, MEK2 or MEK1/2) inhibitor.

In another embodiment, the present invention refers to the use of the dual Aurora kinase/MEK inhibitors of this invention in the treatment of subsets of cancer which are insensitive to the treatment with a selective Aurora kinase (particularly Aurora B kinase) inhibitor.

In another embodiment, the present invention refers to the use of the dual Aurora kinase/MEK inhibitors of this invention in the treatment of subsets of cancer with sensitivity to or dependence on MEK-signalling pathway (particularly such subsets of cancer with one or more mutations in the BRAF or RAS (e.g. KRAS or NRAS) gene) and which are insensitive to the treatment with a selective MEK (MEK1, MEK2 or MEK1/2) inhibitor.

The present invention further refers to the dual Aurora kinase/MEK inhibitors of this invention for use in causing cell death and/or tumor regression in the tumors treated, particularly in those tumors responsive to MEK-signalling pathway, particularly tumors with one or more mutations in the BRAF or RAS (e.g. KRAS and/or NRAS) gene, for example such tumors having one or more of those mutations indicated herein.

The present invention further refers to the dual Aurora kinase/MEK inhibitors of this invention for use in causing apoptosis, senescence and/or polyploidy in the tumors treated, particularly in those tumors responsive to MEK-signalling pathway, in particular tumors with one or more mutations in the BRAF or RAS (e.g. KRAS and/or NRAS) gene.

Further, the dual Aurora kinase/MEK inhibitors of the invention are also useful as dual inhibitors of cell cycle (mitotic checkpoint) and signal transduction in cancer.

The present invention also relates to dual Aurora kinase/MEK inhibitors as described herein for use in the treatment of cancers that are sensitive to the MEK-signalling pathway.

The present invention further relates to dual Aurora kinase/MEK inhibitors as described herein for use in the treatment of cancers (tumors) in which MEK (MEK1 and/or MEK2) is activated.

The present invention further relates to dual Aurora kinase/MEK inhibitors as described herein for use in the treatment of cancers (tumors) in which BRAF or RAS (e.g. KRAS and/or NRAS) is mutated.

The present invention further relates to dual Aurora kinase/MEK inhibitors as described herein for use in the treatment of cancers (tumors) in which BRAF is mutated.

The present invention further relates to dual Aurora kinase/MEK inhibitors as described herein for use in the treatment of cancers (tumors) in which KRAS is mutated.

The present invention further relates to dual Aurora kinase/MEK inhibitors as described herein for use in the treatment of cancers (tumors) in which NRAS is mutated.

The present invention further relates to dual Aurora kinase/MEK inhibitors as described herein for use in the treatment of cancers (tumors) comprising one or more of the following mutations:

BARF mutation in codons 464-469 and/or, particularly, in codon V600, such as e.g. a mutation selected from V600E, V600G, V600A and V600K, or a mutation selected from V600E, V600D, V600K and V600R, or a mutation selected from V600E, V600D and V600K, or a mutation selected from V600E, V600D, V600M, V600G, V600A, V600R and V600K; KRAS mutation in codon 12 (exon 1), codon 13 (exon 1) and/or codon 61 (exon 2), particularly in codons 12 and/or 13, such as e.g. a mutation selected from Gly12Asp, Gly12Val, Gly13Asp, Gly12Cys, Gly12Ser, Gly12Ala and Gly12Arg, or a mutation selected from 12D, 12V, 12C, 12A, 12S, 12R, 12F, 13D, 13C, 13R, 13S, 13A, 13V, 13I, 61H, 61L, 61R, 61K, 61E and 61P;

NRAS mutation in codons 12, 13 and/or 61, such as e.g. a mutation selected from p.G12D, p.G12S, p.G12C, p.G12V, p.G12A, p.G13D, p.G13R, p.G13C, p.G13A, p.Q61R, p.Q61K, p.Q61L, p.Q61H and p.Q61P.

The present invention further relates to dual Aurora kinase/MEK inhibitors as described herein for use in the treatment of cancers (tumors) comprising one or more of the following mutations:

BARF mutation in codons 464-469 and/or, particularly, in codon V600, such as e.g. a mutation selected from V600E, V600D, V600G, V600A, V600R, V600M and V600K.

The present invention further relates to dual Aurora kinase/MEK inhibitors as described herein for use in the treatment of cancers (tumors) comprising one or more of the following mutations:

KRAS mutation in codons 12, 13 and/or 61, particularly in codons 12 and/or 13, such as e.g. a mutation selected from Gly12Asp, Gly12Val, Gly13Asp, Gly12Cys, Gly12Ser, Gly12Ala and Gly12Arg; or a mutation selected from 12D, 12V, 12C, 12A, 12S, 12R, 12F, 13D, 13C, 13R, 13S, 13A, 13V, 13I, 61H, 61L, 61R, 61K, 61E and 61P.

The present invention further relates to dual Aurora kinase/MEK inhibitors as described herein for use in the treatment of cancers (tumors) comprising one or more of the following mutations:

NRAS mutation in codons 12, 13 and/or 61, such as e.g. a mutation selected from p.G12D, p.G12S, p.G12C, p.G12V, p.G12A, p.G13D, p.G13R, p.G13C, p.G13A, p.Q61R, p.Q61K, p.Q61L, p.Q61H and p.Q61P.

The dual Aurora kinase/MEK inhibitors as described herein are active in BRAF and/or RAS mutated cancers. This offers a broad spectrum of indications and subpopulations. Particular cancer indications for the compounds of this invention includes the following:

Melanoma: high BRAF (~43%) and NRAS (~20%) mutation status,
CRC: substantial mutation rate (37% KRAS, 11% BRAF), Pancreas: KRAS mutation status ~70%, high unmet need, NSCLC: moderate KRAS mutation rate (18%).

Further, the present invention relates to a dual Aurora kinase/MEK inhibitor as defined herein for use in the treatment and/or prevention of cancer (particularly a cancer selected from those cancers described hereinabove or hereinbelow) in a patient whose cancer is sensitive to MEK signalling pathway or in whose cancer MEK is activated, such as e.g. in a patient whose cancer has one or more mutations in BRAF or RAS (e.g. KRAS and/or NRAS), such as e.g. one or more of those mutations described herein.

Further, the present invention relates to a dual Aurora kinase/MEK inhibitor as defined herein for use in the treatment and/or prevention of cancer (such as e.g. CRC, PAC, NSCLC or melanoma) in a patient whose cancer cells are characterized by a heterozygous or homozygous BRAF or RAS (e.g. KRAS and/or NRAS) mutational genotype.

Further, the present invention relates to a dual Aurora kinase/MEK inhibitor as defined herein for use in the treatment and/or prevention of cancer (such as e.g. CRC, PAC, NSCLC or melanoma) in a patient whose cancer cells are characterized by a wildtype genotype.

In an embodiment, the present invention relates to a dual Aurora kinase/MEK inhibitor as defined herein for use in the treatment and/or prevention of colorectal cancer (CRC), such as having one or more mutations in KRAS (e.g. in codons 12, 13 and/or 61, particularly in codons 12 and/or 13, such as a mutation selected from Gly12Asp, Gly12Val, Gly13Asp, Gly12Cys, Gly12Ser, Gly12Ala and Gly12Arg; or a mutation selected from 12D, 12V, 12C, 12A, 12S, 12R, 12F, 13D, 13C, 13R, 13S, 13A, 13V, 13I, 61H, 61L, 61R, 61K, 61E and 61P).

In a further embodiment, the present invention relates to a dual Aurora kinase/MEK inhibitor as defined herein for use in the treatment and/or prevention of colorectal cancer (CRC), such as having one or more mutations in BRAF (e.g. in codons 464 to 469 and/or, particularly in codon V600, such as a mutation selected from V600E, V600D, V600G, V600A, V600R and V600K, or a mutation selected from V600E, V600D, V600G, V600A, V600R, V600M and V600K).

In a further embodiment, the present invention relates to a dual Aurora kinase/MEK inhibitor as defined herein for use in the treatment and/or prevention of colorectal cancer (CRC), such as of wildtype genotype.

In a further embodiment, the present invention relates to a dual Aurora kinase/MEK inhibitor as defined herein for use in the treatment and/or prevention of colorectal cancer (CRC), such as of KRAS wildtype genotype.

In a further embodiment, the present invention relates to a dual Aurora kinase/MEK inhibitor as defined herein for use in the treatment and/or prevention of pancreatic cancer (PAC), such as having one or more mutations in KRAS (e.g. in codons 12, 13 and/or 61, particularly in codons 12 and/or 13, such as a mutation selected from Gly12Asp, Gly12Val, Gly13Asp, Gly12Cys, Gly12Ser, Gly12Ala and Gly12Arg; or a mutation selected from 12D, 12V, 12C, 12A, 12S, 12R, 12F, 13D, 13C, 13R, 13S, 13A, 13V, 13I, 61H, 61L, 61R, 61K, 61E and 61P).

In a further embodiment, the present invention relates to a dual Aurora kinase/MEK inhibitor as defined herein for use in the treatment and/or prevention of pancreatic cancer (PAC), such as of KRAS wildtype genotype.

In a further embodiment, the present invention relates to a dual Aurora kinase/MEK inhibitor as defined herein for use in the treatment and/or prevention of pancreatic cancer (PAC), such as regardless of KRAS mutation status.

In a further embodiment, the present invention relates to a dual Aurora kinase/MEK inhibitor as defined herein for use in the treatment and/or prevention of malignant melanoma, such as having one or more mutations in BRAF (e.g. in codons 464 to 469 and/or, particularly in codon V600, such as a mutation selected from V600E, V600D, V600G, V600A, V600R and V600K, or a mutation selected from V600E, V600D, V600G, V600A, V600R, V600M and V600K).

In a further embodiment, the present invention relates to a dual Aurora kinase/MEK inhibitor as defined herein for use in the treatment and/or prevention of malignant melanoma, such as having one or more mutations in NRAS (e.g. in codons 12, 13 and/or 61, such as e.g. a mutation selected from p.G12D, p.G12S, p.G12C, p.G12V, p.G12A, p.G13D, p.G13R, p.G13C, p.G13A, p.Q61R, p.Q61K, p.Q61L, p.Q61H and p.Q61P).

In a further embodiment, the present invention relates to a dual Aurora kinase/MEK inhibitor as defined herein for use in the treatment and/or prevention of malignant melanoma, such as of wildtype genotype.

In a further embodiment, the present invention relates to a dual Aurora kinase/MEK inhibitor as defined herein for use in the treatment and/or prevention of malignant melanoma, such as of BRAF wildtype genotype.

In a further embodiment, the present invention relates to a dual Aurora kinase/MEK inhibitor as defined herein for use in the treatment and/or prevention of non-small cell lung cancer (NSCLC), such as having one or more mutations in KRAS (e.g. in codons 12, 13 and/or 61, particularly in codons 12 and/or 13, such as a mutation selected from Gly12Asp, Gly12Val, Gly13Asp, Gly12Cys, Gly12Ser, Gly12Ala and Gly12Arg; or a mutation selected from 12D, 12V, 12C, 12A, 12S, 12R, 12F, 13D, 13C, 13R, 13S, 13A, 13V, 13I, 61H, 61L, 61R, 61K, 61E and 61P).

Accordingly, particular cancer types amenable for the therapy of this invention are selected from:

colorectal cancer (CRC), especially CRC harboring one or more KRAS mutations; pancreatic cancer (PAC), especially PAC harboring one or more KRAS mutations or PAC harboring KRAS wildtype;

melanoma, especially melanoma harboring one or more BRAF mutations; and non-small-cell lung cancer (NSCLC) especially NSCLC harboring one or more KRAS mutations.

In a particular embodiment, a dual Aurora kinase/MEK inhibitor of this invention, or a composition thereof, is useful for treating patients having colorectal cancer (CRC, including metastatic CRC), especially those CRC patients whose tumor harbors one or more KRAS mutations; such as e.g. as third line treatment, for example after failure of at least two lines of standard chemotherapy (e.g. oxaliplatin-based regimens and irinotecan-based regimens); optionally in combination with one or more other anti-cancer agents.

In another embodiment, a dual Aurora kinase/MEK inhibitor of this invention, or a composition thereof, is useful for treating patients having colorectal cancer (CRC, including metastatic CRC), especially those CRC patients whose tumor harbors KRAS wildtype; such as e.g. as third line treatment, for example after failure of standard chemotherapy (e.g. oxaliplatin-based regimens or irinotecan-based regimens) and EGFR targeted therapy (e.g. cetuximab or panitumumab based regimens); optionally in combination with one or more other anti-cancer agents.

In a particular embodiment, a dual Aurora kinase/MEK inhibitor of this invention, or a composition thereof, is useful for treating patients having pancreatic cancer (PAC, including metastatic, advanced or unresectable PAC), especially those PAC patients whose tumor harbors one or more KRAS mutations; such as e.g. as first line treatment; optionally in combination with one or more other anti-cancer agents.

In a particular embodiment, a dual Aurora kinase/MEK inhibitor of this invention, or a composition thereof, is useful for treating patients having pancreatic cancer (PAC, including metastatic, advanced or unresectable PAC), especially those PAC patients whose tumor harbors KRAS wildtype; such as e.g. as first line treatment; optionally in combination with one or more other anti-cancer agents.

In a particular embodiment, a dual Aurora kinase/MEK inhibitor of this invention, or a composition thereof, is useful for treating patients having melanoma (including metastatic melanoma), especially those melanoma patients whose tumor harbors one or more BRAF mutations; such as e.g. as first line treatment; optionally in combination with one or more other anti-cancer agents.

In another embodiment, a dual Aurora kinase/MEK inhibitor of this invention, or a composition thereof, is useful for treating patients having metastatic melanoma (including metastatic melanoma), especially those melanoma patients whose tumor harbors BRAF wildtype; such as e.g. as first line treatment; optionally in combination with one or more other anti-cancer agents.

In another embodiment, a dual Aurora kinase/MEK inhibitor of this invention, or a composition thereof, is useful for treating patients having melanoma (including metastatic melanoma), especially those melanoma patients whose tumor harbors one or more BRAF mutations; such as e.g. as first or second line treatment; optionally in combination with one or more other anti-cancer agents (e.g. including a Braf inhibitor such as vemurafenib or dabrafenib, optionally with or without a MEK inhibitor such as selumetinib or GSK-1120212).

In another embodiment, a dual Aurora kinase/MEK inhibitor of this invention, or a composition thereof, is useful for treating patients having melanoma (including metastatic melanoma), especially those melanoma patients whose tumor harbors one or more NRAS mutations; optionally in combination with one or more other anti-cancer agents.

Further the present invention relates to a dual Aurora kinase/MEK inhibitor as defined herein for use in anti-cancer therapy as described herein, Further the present invention relates to the use of a dual Aurora kinase/MEK inhibitor as defined herein, optionally in combination with one or more other anti-cancer agents as described herein, for preparing a pharmaceutical composition for use in the treatment and/or prevention of cancer diseases as described herein.

Further the present invention relates to a dual Aurora kinase/MEK inhibitor as defined herein for use in the treatment and/or prevention of cancer diseases as described herein, optionally in combination with one or more other anti-cancer agents as described herein.

Further the present invention relates to a method of treating and/or preventing of cancer diseases as described herein comprising administering a therapeutically effective amount of a dual Aurora kinase/MEK inhibitor as defined herein, and, optionally, one or more other anti-cancer agents as described herein, to the patient in need thereof.

Further, the present invention relates to a method for determining the responsiveness of a mammalian (particularly human) tumor cell (particularly a cell of a tumor selected from those tumors described hereinabove or hereinbelow, such as e.g. melanoma, CRC, pancreatic cancer or NSCLC tumor cell) to the treatment with a dual Aurora kinase/MEK inhibitor as defined herein, said method comprising determining the presence of at least one mutation in the BRAF or RAS (e.g. KRAS and/or NRAS) gene in said tumor cell, wherein said mutation is indicative of whether the cell is likely to respond or is responsive to the treatment (e.g. for undergoing cell death or for inhibiting cell proliferation).

Further, the present invention relates to a method for assessing the efficacy of a dual Aurora kinase/MEK inhibitor as defined herein for treating a cancer (particularly a cancer selected from those cancers described hereinabove or hereinbelow, such as e.g. melanoma, CRC, pancreatic cancer or NSCLC) in a patient in need thereof, said method comprising
 testing that patient's cancer is responsive to MEK signalling pathway or that MEK is activated in patient's cancer,
  particularly determining the presence of at least one mutation in the BRAF or RAS (e.g. KRAS and/or NRAS) gene (such as e.g. one or more of those mutations described herein) in a patient derived tumor tissue sample, wherein said presence indicates that treatment with the dual Aurora kinase/MEK inhibitor is efficacious (e.g. for causing tumor cell death and/or tumor regression).

Further, the present invention relates to a method for determining an increased likelihood of pharmacological effectiveness of treatment by a dual Aurora kinase/MEK inhibitor as defined herein (optionally in combination with one or more other anti-cancer agents) in an individual diagnosed with cancer (particularly a cancer selected from those cancers described hereinabove or hereinbelow, such as e.g. melanoma, CRC, pancreatic cancer or NSCLC), said method comprising
 subjecting a nucleic acid sample from a cancer (tumor) sample from the individual to BRAF or RAS (e.g. KRAS or NRAS) mutational testing or PCR, wherein the presence of at least one mutation in the BRAF or RAS (e.g. KRAS and/or NRAS) gene, such as e.g. one or more of those mutations described herein, indicates an increased likelihood of pharmacological effectiveness of the treatment.

Further, the present invention relates to a dual Aurora kinase/MEK inhibitor as defined herein for use in a method of treatment of cancer (particularly a cancer selected from those cancers described hereinabove or hereinbelow, such as e.g. melanoma, CRC, pancreatic cancer or NSCLC) in a patient in need thereof, said method comprising
 testing whether patient's cancer is responsive to MEK signalling pathway or whether MEK is activated in patient's cancer, particularly testing for one or more mutations in BRAF or RAS (e.g. KRAS and/or NRAS) gene in patient's tumor (such as e.g. for one or more of those mutations described herein), and
 administering the dual Aurora kinase/MEK inhibitor, optionally in combination with one or more other anti-cancer agents, to the patient.

Further, the present invention relates to a method of identifying a patient for eligibility for cancer therapy comprising a dual Aurora kinase/MEK inhibitor as defined herein (optionally in combination with one or more other anti-cancer agents), said method comprising
 providing a tumor tissue sample from a patient, particularly from a patient with a cancer e.g. selected from melanoma, CRC, pancreatic cancer and NSCLC;
 determining whether patient's cancer is responsive to MEK signalling pathway or whether MEK is activated in patient's cancer,
  particularly determining the presence of at least one mutation in the BRAF or RAS (e.g. KRAS and/or NRAS) gene (such as e.g. one or more of those mutations described herein) in patient's tumor tissue sample;

identifying the patient as eligible to receive the cancer therapy where the patient's cancer is determined as being responsive to MEK signalling pathway or MEK is determined as being activated in patient's cancer, particularly where the patient's tumor tissue sample is determined as having at least one mutation in the BRAF or RAS (e.g. KRAS and/or NRAS) gene (such as e.g. one or more of those mutations described herein).

Further, the present invention relates to a method of treating cancer (e.g. melanoma, CRC, pancreatic cancer or NSCLC) comprising identifying a cancer patient as described herein and administering an effective amount of the dual Aurora kinase/MEK inhibitor as defined herein (optionally in combination with one or more other anti-cancer agents) to said patient.

Further, the present invention relates to a method of treating a mammal (particular human) patient having cancer (particularly a cancer selected from those cancers described hereinabove or hereinbelow, such as e.g. melanoma, CRC, pancreatic cancer or NSCLC), said method comprising:

obtaining a nucleic acid sample from a cancer sample from said patient;

determining whether patient's cancer is responsive to MEK signalling pathway or whether MEK is activated in patient's cancer, particularly subjecting the sample to BRAF or RAS (e.g. KRAS and/or NRAS) mutational testing or PCR and identifying the presence of at least one mutation in the BRAF or RAS (e.g. KRAS and/or NRAS) gene (such as e.g. one or more of those mutations described herein); and administering an effective amount of a dual Aurora kinase/MEK inhibitor as defined herein (optionally in combination with one or more other anti-cancer agents) to the patient whose cancer is determined as being responsive to MEK signalling pathway or in whose cancer MEK is determined as being activated, particularly to the patient in whose sample the presence of at least one mutation in the BRAF or RAS (e.g. KRAS and/or NRAS) gene (such as e.g. one or more of those mutations described herein) is identified.

Further, the present invention relates to a method of treatment comprising a) identifying a patient (particular human patient) in need of treatment for cancer (e.g. advanced solid tumor), such as e.g. colorectal cancer (CRC), pancreatic cancer (PAC), melanoma or non-small-cell lung cancer (NSCLC), b) determining that patient's cancer is responsive to MEK signalling pathway or that in patient's cancer the MAPK pathway is hyperactivated, particularly determining that patient's cancer harbors one or more mutations in BRAF or RAS (e.g. KRAS and/or NRAS) gene (such as e.g. one or more of those mutations described herein), c) administering a therapeutically effective amount of a dual Aurora kinase/MEK inhibitor as defined herein (optionally in combination with one or more other anti-cancer agents) to the patient.

Further, the present invention relates to a method of treatment comprising a) identifying a patient (particular human patient) in need of treatment for colorectal cancer (CRC, e.g. metastatic CRC), b) determining that patient's tumor harbors one or more mutations in KRAS gene (such as e.g. one or more of those mutations described herein), c) administering a therapeutically effective amount of a dual Aurora kinase/MEK inhibitor as defined herein (optionally in combination with one or more other anti-cancer agents) to the patient.

Further, the present invention relates to a method of treatment comprising a) identifying a patient (particular human patient) in need of treatment for colorectal cancer (CRC, e.g. metastatic CRC), b) determining that patient's tumor harbors KRAS wild type gene, c) administering a therapeutically effective amount of a dual Aurora kinase/MEK inhibitor as defined herein (optionally in combination with one or more other anti-cancer agents) to the patient.

Further, the present invention relates to a method of treatment comprising a) identifying a patient (particular human patient) in need of treatment for pancreatic cancer (PAC, e.g. metastatic, unresectable or locally advanced PAC), b) determining that patient's tumor harbors one or more mutations in KRAS gene (such as e.g. one or more of those mutations described herein), c) administering a therapeutically effective amount of a dual Aurora kinase/MEK inhibitor as defined herein (optionally in combination with one or more other anti-cancer agents) to the patient.

Further, the present invention relates to a method of treatment comprising a) identifying a patient (particular human patient) in need of treatment for pancreatic cancer (PAC, e.g. metastatic, unresectable or locally advanced PAC), b) determining that patient's tumor harbors KRAS wild type gene, c) administering a therapeutically effective amount of a dual Aurora kinase/MEK inhibitor as defined herein (optionally in combination with one or more other anti-cancer agents) to the patient.

Further, the present invention relates to a method of treatment comprising a) identifying a patient (particular human patient) in need of treatment for melanoma (e.g. metastatic melanoma), b) determining that patient's tumor harbors one or more mutations in BRAF gene (such as e.g. one or more of those mutations described herein), c) administering a therapeutically effective amount of a dual Aurora kinase/MEK inhibitor as defined herein (optionally in combination with one or more other anti-cancer agents) to the patient.

Further, the present invention relates to a method of treatment comprising a) identifying a patient (particular human patient) in need of treatment for melanoma (e.g. metastatic melanoma), b) determining that patient's tumor harbors BRAF wild type gene, c) administering a therapeutically effective amount of a dual Aurora kinase/MEK inhibitor as defined herein (optionally in combination with one or more other anti-cancer agents) to the patient.

In certain embodiments, within therapy according to this invention, a particular subpopulation of patients with colorectal cancer (CRC) according to this invention refers to such (metastatic) CRC patients who failed at least two lines of standard chemotherapy (e.g. oxaliplatin-based regimens and irinotecan-based regimens).

In a further embodiment of this invention, a further particular subpopulation of patients with colorectal cancer (CRC) according to this invention refers to such (metastatic) CRC patients whose CRC tumor harbors a mutation in KRAS gene (such as e.g. one or more of those mutations described herein) and who failed at least two lines of standard chemotherapy (e.g. oxaliplatin-based regimens and irinotecan-based regimens).

In other certain embodiments, within therapy according to this invention, a particular subpopulation of patients with colorectal cancer (CRC) according to this invention refers to such (metastatic) CRC patients who failed standard chemotherapy (e.g. oxaliplatin-based regimens or irinotecan-based regimens) and EGFR targeted therapy (e.g. cetuximab or panitumumab based regimens).

In a further embodiment of this invention, a further particular subpopulation of patients with colorectal cancer (CRC) according to this invention refers to such (metastatic) CRC patients whose CRC tumor harbors KRAS wild type gene and who failed standard chemotherapy (e.g. oxaliplatin-based regimens or irinotecan-based regimens) and EGFR targeted therapy (e.g. cetuximab or panitumumab based regimens).

In another embodiment of this invention, a subpopulation of patients with colorectal cancer (CRC) according to this invention refers to such (metastatic) CRC patients who failed to respond to treatment with an EGFR inhibitor (such as e.g. an anti-EGFR antibody such as cetuximab or panitumumab).

In another embodiment of this invention, a subpopulation of patients with colorectal cancer (CRC) according to this invention refers to such (metastatic) CRC patients whose CRC tumor harbors KRAS wild type gene and who failed to respond to treatment with an EGFR inhibitor (such as e.g. an anti-EGFR antibody such as cetuximab or panitumumab).

In another embodiment of this invention, a subpopulation of patients with melanoma according to this invention refers to such (metastatic, advanced or late-stage) melanoma patients who failed to respond to treatment with a BRaf inhibitor (such as e.g. vemurafenib).

In another embodiment of this invention, a subpopulation of patients with melanoma according to this invention refers to such (metastatic, advanced or late-stage) melanoma patients whose melanoma tumor harbors a mutation in BRAF gene (e.g. in BRAF V600, such as e.g. one or more of those mutations described herein, including e.g. V600E) and who failed to respond to treatment with a BRaf inhibitor (such as e.g. vemurafenib or dabrafenib).

Further the present invention relates to the use of a dual Aurora kinase/MEK inhibitor as defined herein for preparing a pharmaceutical composition for use in the anti-cancer therapy as described herein, e.g. for use in a method of treatment of a cancer patient as described hereinabove and hereinbelow, optionally in combination with an other anti-cancer agent.

Further the present invention relates to a dual Aurora kinase/MEK inhibitor as defined herein for use in the anti-cancer therapy as described herein, e.g. for use in a method of treatment of a cancer patient as described hereinabove and hereinbelow, optionally in combination with an other anti-cancer agent.

Examples of mutations in BARF according to this invention may include, without being limited to, a mutation in codons 464-469 and/or, particularly, in codon V600, such as e.g. a mutation selected from V600E, V600G, V600A and V600K, or a mutation selected from V600E, V600D, V600K and V600R, or a mutation selected from V600E, V600D and V600K, or a mutation selected from V600E, V600D, V600M, V600G, V600A, V600R and V600K.

In certain embodiments, particular examples of mutations in BARF according to this invention may include a mutation in V600, especially the V600E mutation.

Examples of mutations in KRAS according to this invention may include, without being limited to, a mutation in codons 12, 13 and/or 61, particularly in codons 12 and/or 13, such as e.g. a mutation selected from Gly12Asp, Gly12Val, Gly13Asp, Gly12Cys, Gly12Ser, Gly12Ala and Gly12Arg; or a mutation selected from 12D, 12V, 12C, 12A, 12S, 12R, 12F, 13D, 13C, 13R, 13S, 13A, 13V, 13I, 61H, 61L, 61R, 61K, 61E and 61P.

In certain embodiments, particular examples of mutations in KRAS according to this invention may include a mutation in codon 12 or 13, especially a mutation selected from 12D, 12V, 12C, 12S, 12A, 12R and 13D Examples of mutations in NRAS according to this invention may include, without being limited to, a mutation in codons 12, 13 and/or 61, such as e.g. a mutation selected from p.G12D, p.G12S, p.G12C, p.G12V, p.G12A, p.G13D, p.G13R, p.G13C, p.G13A, p.Q61R, p.Q61K, p.Q61L, p.Q61H and p.Q61P.

Testing methods on mutations in BRAF or RAS are known to the skilled person. For example, commonly used methods for mutation detection in clinical samples may include or be based on, nucleic acid sequencing (e.g. dideoxy or pyrosequencing), single-strand conformational polymorphism analysis, melt-curve analysis, real-time PCR (such as with melt-curve analysis e.g. using fluorescent probes complementary to the target amplicon, which can be used to distinguish genetic variants by the differences in the melting temperature needed to dissociate probe from target) or allele-specific PCR (such as with various modes used to distinguish mutant from wild-type sequences e.g. using oligonucleotide primers that allow the specific amplification of mutant versus wild-type sequence, such as e.g. using ARMS™ technology. The amplification products may be detected by a variety of methods ranging from gel electrophoresis to real-time PCR, such as e.g. using Scorpion™ technology).

For example, the diagnostic kits for detecting mutations in the BRAF, KRAS or NRAS oncogen may be based on Pyrosequencing, RotorGeneQ™ (Qiagen) or Cobas™ (Roche) technology.

A commercially available diagnostic kit for detecting mutations in the BRAF oncogen is, for example, the TheraScreen™ B-Raf mutation detection kit, particularly for detecting the mutations V600E and V600K, or the Mutector™ B-Raf V600 mutation detection kit, particularly for detecting the mutations V600E, V600A and V600G, or the PyroMark™ B-Raf kit, e.g. for sequencing of codon 600 and codons 464-469.

A commercially available diagnostic kit for detecting mutations in the KRAS oncogen is, for example, the TheraScreen™ K-Ras mutation detection kit, for detecting the mutations 12Ala, 12Asp, 12Arg, 12Cys, 12Ser, 12Val and 13Asp.

A diagnostic kit for detecting mutations in the BRAF oncogen is, for example, the TheraScreen™ BRAF PCR kit by Qiagen, particularly in a version for detecting a mutation selected from V600E, V600D and V600K or in a version for detecting a mutation selected from V600E, V600D, V600K and V600R, or the TheraScreen™ BRAF Pyro kit by Qiagen, e.g. for detecting a mutation selected from V600E, V600A, V600M and V600G.

A diagnostic kit for detecting mutations in the KRAS oncogen is, for example, the TheraScreen™ KRAS PCR kit by Qiagen (e.g. for detecting a mutation selected from G12A, G12D, G12S, G12V, G12R, G12C and G13D), or the PyroMark™ KRAS assay, or the TheraScreen™ KRAS Pyro kit by Qiagen, e.g. for detecting a mutation selected from G12A, G12D, G12S, G12V, G12R, G12C, G13D, Q61H, Q61E and Q61L.

A diagnostic kit for detecting mutations in the NRAS oncogen is, for example, the TheraScreen™ NRAS Pyro or qPCR kit by Qiagen.

Another diagnostic kit for identifying mutations in the KRAS gene is, for example, the Cobas™ KRAS Mutation Test by Roche, which is a real-time PCR test and which can be used for detecting a broad spectrum of mutations in the codons 12, 13 and 61 of the KRAS gene, covering the mutations 12D, 12V, 12C, 12A, 12S, 12R, 12F, 13D, 13C, 13R, 13S, 13A, 13V, 13I, 61H, 61L, 61R, 61K, 61E and 61P.

Another diagnostic kit for identifying a mutation in the BRAF gene is, for example, the Cobas™ BRAF Mutation Test by Roche, which is a real-time PCR test.

For mutational testing a typical cancer (tumor) sample comprising nucleic acid is used, which may be selected from the group consisting of a tissue, a biopsy probe, cell lysate, cell culture, cell line, organ, organelle, biological fluid, blood sample, urine sample, skin sample, and the like. In a particular embodiment, the cancer (tumor) sample comprising nucleic acid is a biopsy probe.

The present invention further provides the use of such a BRAF or RAS mutation kit as companion diagnostic to the dual Aurora kinase/MEK inhibitors of this invention for cancer patients in need thereof, such as e.g. patients having a cancer as descibed herein.

The present invention further provides such kits useful for determining an increased likelihood of effectiveness of treatment by a dual Aurora kinase/MEK inhibitor as defined herein, optionally in combination with one or more other anti-cancer agents, in a mammalian, preferably human, patient diagnosed with cancer (such as e.g. those cancers described herein), said kit preferably comprising means for detecting a mutation in BRAF or RAS (e.g. KRAS and/or NRAS) oncogen, particularly one or more of such mutations described herein.

The term dual Aurora kinase/MEK inhibitor as used herein also comprises any tautomers, pharmaceutically acceptable N-oxides or salts thereof, hydrates and solvates thereof, including the respective crystalline forms.

The dual Aurora kinase/MEK inhibitor compounds of formula (I) according to this invention (including e.g. the dual Aurora kinase/MEK inhibitor compounds 1 to 27 of group A) can be synthesized as described in WO 2010/012747 or analogously or similarly thereto, e.g. as shown in the following reaction scheme, where R1 and R have the meanings as defined above (including e.g. in the compounds 1 to 27) and X denotes a suitable leaving group, such as e.g bromine or iodine. The indolinone intermediate compounds are known or they can be synthesized using standard methods of synthesis or analogously to the methods described in WO 2007/122219 or WO 2008/152013 or as shown by way of example in the following reaction scheme. The propynoic acid amides are known or can be prepared according to standard methods.

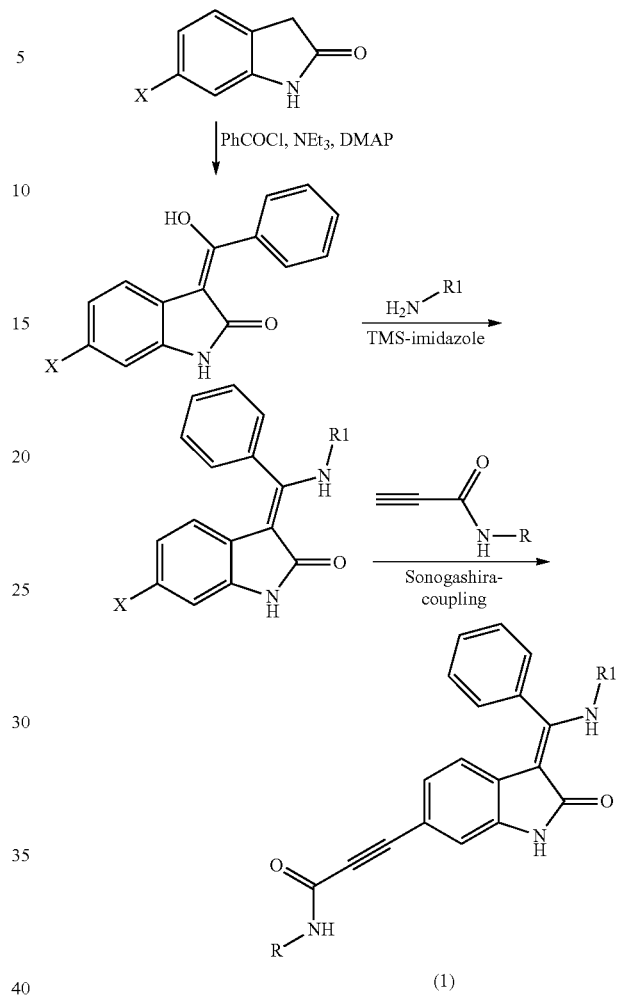

It is moreover known to the person skilled in the art that if there are a number of reactive centers on a starting or intermediate compound it may be necessary to block one or more reactive centers temporarily by protective groups in order to allow a reaction to proceed specifically at the desired reaction center. After the desired reaction has occurred, the protective group is usually removed in a suitable manner. A detailed description for the use of a large number of proven protective groups is found, for example, in "Protective Groups in Organic Synthesis" by T. Greene and P. Wuts (John Wiley & Sons, Inc. 2007, 4th Ed.) or in "Protecting Groups (Thieme Foundations Organic Chemistry Series N Group" by P. Kocienski (Thieme Medical Publishers, 2004).

The compounds of the formula (1) can be converted, optionally, into their N-oxides, for example with the aid of hydrogen peroxide (e.g. in methanol) or with the aid of m-chloroperoxybenzoic acid (e.g. in dichloromethane). The person skilled in the art is familiar on the basis of his/her expert knowledge with the reaction conditions which are specifically necessary for carrying out the N-oxidation.

Depending on the disease diagnosed, improved treatment outcomes may be obtained if a dual Aurora kinase/MEK inhibitor of this invention is combined with one or more other active substances customary for the respective diseases, such as e.g. one or more active substances selected from among the other anti-cancer agents (such as e.g. cytostatic or cytotoxic substances, cell proliferation inhibitors, anti-angiogenic substances, steroids or antibodies), especially those (targeted or non-targeted) anti-cancer agents mentioned herein. Such a combined treatment may be given as a free combination of the substances or in the form of a fixed combination, including kit-of-parts. Pharmaceutical formulations of the combination components needed for this may either be obtained commercially as pharmaceutical compositions or may be formulated by the skilled man using conventional methods.

Within this invention it is to be understood that the combinations, compositions, kits or combined uses according to this invention may envisage the simultaneous, sequential or separate administration of the active ingredients. It will be appreciated that the active components can be administered formulated either dependently or independently, such as e.g. the active components may be administered either as part of the same pharmaceutical composition/dosage form or in separate pharmaceutical compositions/dosage forms.

In this context, "combination" or "combined" within the meaning of this invention includes, without being limited, fixed and non-fixed (e.g. free) forms (including kits) and uses, such as e.g. the simultaneous, concurrent, sequential, successive, alternate or separate use of the components or ingredients.

The administration of the active components may take place by co-administering the active components or ingredients, such as e.g. by administering them simultaneously or concurrently in one single or in two separate formulations or dosage forms. Alternatively, the administration of the active components may take place by administering the active components or ingredients sequentially, successively or in alternation, such as e.g. in two separate formulations or dosage forms.

Other anti-cancer agents which may be administered in combination with the dual Aurora kinase/MEK inhibitor of this invention in the therapies described herein may be selected from the following chemotherapeutic agents:

(i) alkylating or carbamylating agents, such as for example nitrogen mustards (with bis-(2-chlorethyl) grouping) such as e.g. cyclophosphamide (CTX, e.g. Cytoxan, Cyclostin, Endoxan), chlorambucil (CHL, e.g. Leukeran), ifosfamide (e.g. Holoxan) or melphalan (e.g. Alkeran), alkyl sulfonates such as e.g. busulphan (e.g. Myleran), mannosulphan or treosulphan, nitrosoureas such as e.g. streptozocin (e.g. Zanosar) or chloroethylnitrosoureas CENU like carmustine BCNU or lomustine CCNU or fotemustine, hydrazines such as e.g. procarbazine, triazenes/imidazotetrazines such as e.g. dacarbazine (DTIC) or temozolomide (e.g. Temodar), or ethylenimines/aziridines/methylmelamines such as e.g. mitomycin C, thiotepa or altretamine, or the like;

(ii) platinum derivatives, such as for example cisplatin (CisP, e.g. Platinex, Platinol), oxaliplatin (e.g. Eloxatin), satraplatin or carboplatin (e.g. Carboplat), or the like;

(iii) antimetabolites, such as for example folic acid antagonists such as e.g. methotrexate (MTX, e.g. Farmitrexat), raltitrexed (e.g. Tomudex), edatrexate or pemetrexed (e.g. Alimta), purine antagonists such as e.g. 6-mercaptopurine (6MP, e.g. Puri-Nethol), 6-thioguanine, pentostatin, cladribine, clofarabine or fludarabine (e.g. Fludara), or pyrimidine antagonists such as e.g. cytarabine (Ara-C, e.g. Alexan, Cytosar), floxuridine, 5-fluorouracil (5-FU) alone or in combination with leucovorin, tegafur, 5-azacytidine (e.g. Vidaza), capecitabine (e.g. Xeloda), decitabine (e.g. Dacogen) or gemcitabine (e.g. Gemzar), or the like;

(iv) antitumor/cyctotoxic antibiotics, such as for example anthracyclines such as e.g. daunorubicin including its hydrochloride salt (including liposomal formulation), doxorubicin including its hydrochloride and citrate salt (e.g. Adriblastin, Adriamycin, including liposomal formulation like Doxil or Caelyx), epirubicin or idarubicin including its hydrochloride salt (e.g. Idamycin), anthracenediones such as e.g. mitoxantrone (e.g. Novantrone), or *streptomyces* such as e.g. bleomycin, mitomycin or actinomycin D/dactinomycin, or the like;

(v) topoisomerase (including I and II) inhibitors, such as e.g. for example camptothecin and camptothecin analogues such as e.g. irinotecan (e.g. Camptosar) including its hydrochloride, topotecan (e.g. Hycamtin), rubitecan or diflomotecan, epipodophyllotoxins such as e.g. etoposide (e.g. Etopophos) or teniposide, anthracyclines (see above), mitoxantrone, losoxantrone or actinomycin D, or amonafide, or the like;

(vi) microtubule interfering agents, such as for example vinca alkaloids such as e.g. vinblastine (including its sulphate salt), vincristine (including its sulphate salt), vinflunine, vindesine or vinorelbine (including its tartrate salt), taxanes (taxoids) such as e.g. docetaxel (e.g. Taxotere), paclitaxel (e.g. Taxol) or analogues, derivatives or conjugates thereof (e.g. larotaxel), or epothilones such as e.g. epothilone B (patupilone), azaepothilone (ixabepilone), ZK-EPO (sagopilone) or KOS-1584 or analogues, derivatives or conjugates thereof, or the like;

(vii) hormonal therapeutics, such as for example anti-androgens such as e.g. flutamide, nilutamide or bicalutamide (casodex), anti-estrogens such as e.g. tamoxifen, raloxifene or fulvestrant, LHRH agonists such as e.g. goserelin, leuprolide, buserelin or triptolerin; GnRH antagonists such as e.g. abarelix or degarelix; aromatase inhibitors such as e.g. steroids (e.g. exemestane or formestane) or non-steroids (e.g. letrozole, fadrozole or anastrozole).

Further examples of other anti-cancer agents which may be administered in combination with the dual Aurora kinase/MEK inhibitor of this invention in the therapies described herein may include, without being limited to, cell signalling and/or angiogenesis inhibitors.

Cell signalling and/or angiogenesis inhibitors may include, without being limited, agents targeting (e.g. inhibiting) endothelial-specific receptor tyrosine kinase (Tie-2), epidermal growth factor (receptor) (EGF(R)), insulin-like growth factor (receptor) (IGF-(R)), fibroblast growth factor (receptor) (FGF(R)), platelet-derived growth factor (receptor) (PDGF(R)), hepatocyte growth factor (receptor) (HGF(R)), or vascular endothelial growth factor (VEGF) or VEGF receptor (VEGFR); as well as thrombospondin analogs, matrix metalloprotease (e.g. MMP-2 or MMP-9) inhibitors, thalidomide or thalidomide analogs, integrins, angiostatin, endostatin, vascular disrupting agents (VDA), protein kinase C (PKC) inhibitors, and the like.

Particular angiogenesis inhibitors are agents targeting (e.g. inhibiting) vascular endothelial growth factor (VEGF) or VEGF receptor (VEGFR).

Agents targeting (e.g. inhibiting) VEGF/VEGFR relate to compounds which target (e.g. inhibit) one or more members of the VEGF or VEGFR family (VEGFR1, VEGFR2, VEGFR3) and include inhibitors of any vascular endothelial growth factor (VEGF) ligand (such as e.g. ligand antibodies or soluble receptors) as well as inhibitors of any VEGF receptor (VEGFR) (such as e.g. VEGFR tyrosin kinase inhibitors, VEGFR antagonists or receptor antibodies).

A VEGFR inhibitor is an agent that targets one or more members of the family of vascular endothelial growth factor (VEGF) receptor, particularly of the VEGFR family of tyrosine kinases (either as single kinase inhibitor or as multikinase inhibitor), including small molecule receptor tyrosine kinase inhibitors and anti-VEGFR antibodies.

Examples of small molecule VEGFR inhibitors include, without being limited to, sorafenib (Nexavar, also an inhibitor of Raf, PDGFR, Flt3, Kit and RETR), sunitinib (Sutent, also inhibitor of Kit, Flt3 and PDGFR), pazopanib (GW-786034, also inhibitor of Kit and PDGFR), cediranib (Recentin, AZD-2171), axitinib (AG-013736, also inhibitor of PDGFR and Kit), vandetanib (Zactima, ZD-6474, also inhibitor of EGFR and Ret), vatalanib (also inhibitor of PDGFR and Kit), motesanib (AMG-706, also inhibitor of PDGFR and Kit), brivanib (also FGFR inhibitor), linifanib (ABT-869, also inhibitor of PDGFR, Flt3 and Kit), tivozanib (KRN-951, also inhibitor of PDGFR, Kit, and MAP), E-7080 (also inhibitor of Kit and Kdr), regorafenib (BAY-73-4506, also inhibitor of Tek), foretinib (XL-880, also inhibitor of Flt3, Kit and Met), telatinib (BAY-57-9352), MGCD-265 (also inhibitor of c-MET, Tie2 and Ron), dovitinib (also inhibitor of PDGFR, Flt3, Kit and FGFR), nintedanib (also inhibitor of FGFR and PDGFR), XL-184 (cabozantinib, also inhibitor of Met, Flt3, Ret, Tek and Kit).

Examples of biological entities inhibiting VEGF(R) include, without being limited to, anti-VEGF ligand antibodies such as e.g. bevacizumab (Avastin); soluble receptors such as aflibercept (VEGF-Trap); anti-VEGF receptor antibodies such as e.g. ramucirumab (IMC-1121b) or IMC-18F1; VEGFR antagonists such as e.g. CT-322 or CDP-791.

Examples of small molecule VEGFR-1 (Flt-1) inhibitors include, without being limited to, sunitinib, cediranib and dovitinib.

Examples of small molecule VEGFR-2 (Flk-1, Kdr) inhibitors include, without being limited to, sorafenib, sunitinib, cediranib and dovitinib.

Examples of small molecule VEGFR-3 (Flt-4) inhibitors include, without being limited to, sorafenib, sunitinib and cediranib.

Agents targeting (e.g. inhibiting) PDGFR relate to compounds which target (e.g. inhibit) one or more members of the PDGFR family and include inhibitors of a platelet-derived growth factor receptor (PDGFR) family tyrosin kinase (either as single kinase inhibitor or as multikinase inhibitor) as well as anti-PDGFR antibodies.

A PDGFR inhibitor is an agent that targets one or more members of the PDGFR family, particularly of the PDGFR family of tyrosine kinases (either as single kinase inhibitor or as multikinase inhibitor), including small molecule receptor tyrosine kinase inhibitors and anti-PDGFR antibodies.

Examples of small molecule PDGFR inhibitors include, without being limited to, nintedanib (also inhibitor of VEGFR and FGFR), axitinib (also inhibitor of VEGFR and Kit), dovitinib (also inhibitor of VEGFR, Flt3, Kit and FGFR), sunitinib (also inhibitor of VEGFR, Flt3 and Kit), motesanib (also inhibitor of VEGFR and Kit), pazopanib (also inhibitor of VEGFR and Kit), nilotinib (also inhibitor of Abl and Kit), tandutinib (also inhibitor of Flt3 and Kit), vatalanib (also inhibitor of VEGFR and Kit), tivozanib (KRN-951, also inhibitor of VEGFR, Kit, and MAP), AC-220 (also inhibitor of Flt3 and Kit), TSU-68 (also inhibitor of FGFR and VEGFR), KRN-633 (also inhibitor of VEGFR, Kit and Flt3), linifinib (also inhibitor of Flt3, Kit and VEGFR), sorafenib (Nexavar, also an inhibitor of Raf, VEGFR, Flt3, Kit and RETR), imatinib (Glevec, also inhibitor of Abl and Kit). Examples of anti-PDGFR antibodies include, without being limited to, IMC-3G3.

Agents targeting FGFR relate to compounds which target one or more members of the FGFR family and include inhibitors of a fibroblast growth factor receptor family tyrosin kinase (either as single kinase inhibitor or as multikinase inhibitor).

A FGFR inhibitor is an agent that targets one or more members of the FGFR family (e.g. FGFR1, FGFR2, FGFR3), particularly of the FGFR family of tyrosine kinases (either as single kinase inhibitor or as multikinase inhibitor), including small molecule receptor tyrosine kinase inhibitors and anti-FGFR antibodies.

Examples of small molecule FGFR inhibitors include, without being limited to, nintedanib (also inhibitor of VEGFR and PDGFR), dovitinib (also inhibitor of VEGFR, Flt3, Kit and PDGFR), KW-2449 (also inhibitor of Flt3 and Abl), brivanib (also VEGFR inhibitor), TSU-68 (also inhibitor of PDGFR and VEGFR).

Agents targeting (e.g. inhibiting) EGFR relate to compounds which target (e.g. inhibit) one or more members of the epidermal growth factor receptor family (erbB1, erbB2, erbB3, erbB4) and include inhibitors of one or more members of the epidermal growth factor receptor (EGFR) family kinases (either as single kinase inhibitor or as multikinase inhibitor) as well as antibodies binding to one or more members of the epidermal growth factor receptor (EGFR) family.

A EGFR inhibitor is an agent that targets one or more members of the EGFR family, particularly of the EGFR family of tyrosine kinases (either as single kinase inhibitor or as multikinase inhibitor), including small molecule receptor tyrosine kinase inhibitors and anti-EGFR antibodies.

Examples of small molecule epidermal growth factor receptor (EGFR) inhibitors include, without being limited to, erlotinib (Tarceva), gefitinib (Iressa), afatinib, lapatinib (Tykerb), vandetanib (Zactima, also inhibitor of VEGFR and RETR), neratinib (HKI-272), varlitinib, AZD-8931, AC-480, AEE-788 (also inhibitor of VEGFR).

Examples of antibodies against the epidermal growth factor receptor (EGFR) include, without being limited to, the anti-ErbB1 antibodies cetuximab, panitumumab or nimotuzumab, the anti-ErbB2 antibodies trastuzumab (Herceptin), pertuzumab (Omnitarg) or ertumaxomab, and the anti-EGFR antibody zalutumumab.

EGFR inhibitors in the meaning of this invention may refer to reversible EGFR tyrosine kinase inhibitors, such as e.g. gefitinib, erlotinib, vandetanib or lapatinib, or to irreversible EGFR tyrosin kinase inhibitors, such as e.g. neratinib or PF-299804.

EGFR inhibitors in the meaning of this invention may refer to erbB selective inhibitors, such as e.g. erbB1 inhibitors (e.g. erlotinib, gefitinib, cetuximab, panitumumab), or erbB2 inhibitors (e.g. trastuzumab), dual erbB1/erbB2 inhibitors (e.g. lapatinib, afatinib) or pan-erbB inhibitors (e.g. PF-299804).

IGF(R) inhibitors are agents that target one or more members of the insulin-like growth factor (IGF) family (e.g. IGF1 and/or IGF2), particularly of the IGFR family of tyrosine kinases, e.g. IGFR-1 (either as single kinase inhibitor or as multikinase inhibitor), and/or of insulin receptor pathways, and may include, without being limited to, the IGFR tyrosin kinase inhibitors OSI-906 (linsitinib) and 1-{4-[(5-cyclopropyl-1H-pyrazol-3-yl)amino]pyrrolo[2,1-f][1,2,4]triazin-2-yl}-N-(6-fluoro-3-pyridinyl)-2-methyl-L-prolinamide (BMS-754807), as well as the anti-IGF(R) antibodies figitumumab, cixutumumab, dalotuzumab, ganitumab and robatumumab.

HGF(R) inhibitors are agents that target one or more members of the hepatocyte growth factor (HGF) family, particularly of the HGFR family of tyrosine kinases (either as single kinase inhibitor or as multikinase inhibitor), and may include, without being limited to, the HGFR tyrosin kinase inhibitors cabozantinib (XL-184, also inhibitor of VEGFR, Flt3, Ret, Tek and Kit), crizotinib (also inhibitor of Alk), foretinib (aslo inhibitor of Flt3, Kit and VEGFR) and tivantinib, as well as the anti-HGF(R) antibodies ficlatuzumab and onartuzumab.

Vascular targeting agents (VTAs) may include, without being limited to, vascular damaging or disrupting agents such as e.g. 5,6-dimethylxanthenone-4-acetic acid (DMXAA, vadimezan), combretastatin A4 phosphate (Zybrestat) or combretastatin A4 analogues, such as e.g. ombrabulin (AVE-8062).

Thrombospondin analogs may include, without being limited to, ABT-510, and the like.

Matrix metalloprotease (MMP) inhibitors may include, without being limited to, marimastat, and the like.

PKC inhibitors are agents that inhibit one or more members of the protein kinase C (PKC) family (either as single kinase inhibitor or as multikinase inhibitor) and may include, without being limited to, enzastaurin, bryostatin and midostaurin.

A angiogenesis inhibitor for use in combination therapy of this invention may be selected from bevacizumab (Avastin), aflibercept (VEGF-Trap), vandetanib, cediranib, axitinib, sorafenib, sunitinib, motesanib, vatalanib, pazopanib, dovitinib and nintedanib.

A particular angiogenesis inhibitor for administration in conjunction with a dual Aurora kinase/MEK inhibitor of this invention is nintedanib.

Accordingly, in an embodiment, a cell signalling and/or angiogenesis inhibitor of this invention refers preferably to an angiogenesis inhibitor, such as e.g. an agent targeting VEGF or VEGFR.

In a particular embodiment, an angiogenesis inhibitor or VEGFR inhibitor within the meaning of this invention is nintedanib (BIBF 1120) having the formula

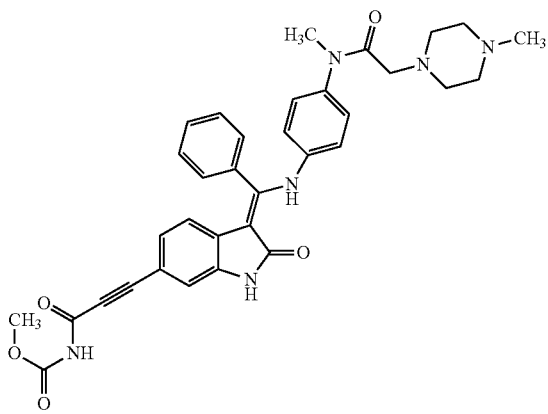 [SMILES: COC(=O)NC(=O)C#Cc1ccc2c(c1)NC(=O)/C2=C(\Nc1ccc(N(C)C(=O)CN2CCN(C)CC2)cc1)c1ccccc1]

optionally in the form of a tautomer or pharmaceutically acceptable salt thereof (e.g. hydroethanesulphonate).

A dual Aurora kinase/MEK inhibitor of this invention may also be successfully administered in conjunction with an inhibitor of the erbB1 receptor (EGFR) and erbB2 (Her2/neu) receptor tyrosine kinases, particularly afatinib.

Accordingly, in a further embodiment, a cell signalling and/or angiogenesis inhibitor of this invention refers preferably to a cell signalling inhibitor, such as e.g. an agent targeting EGFR, for example a dual irreversible EGFR/Her2 inhibitor.

In a particular embodiment, a cell signalling inhibitor or EGFR inhibitor (particularly dual irreversible EGFR/Her2 inhibitor) within the meaning of this invention is afatinib (BIBW 2992) having the formula

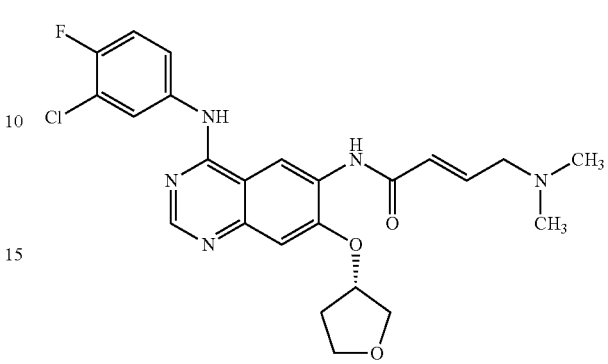

optionally in the form of a tautomer or pharmaceutically acceptable salt thereof.

Yet further examples of other anti-cancer agents which may be administered in combination with the dual Aurora kinase/MEK inhibitor of this invention in the therapies described herein may include, without being limited to, histone deacetylase inhibitors, proteasome inhibitors, HSP90 inhibitors, kinesin spindle protein inhibitors, cyclooxygenase inhibitors, bisphosphonates, biological response modifiers (e.g. cytokines such as IL-2, or interferones such as interferon-gamma), antisense oligonucleotides, Toll-like receptor agonists, deltoids or retinoids, Abl inhibitors or Bcr-Abl inhibitors, Src inhibitors, FAK inhibitors, JAK/STAT inhibitors, inhibitors of the PI3K/PDK1/AKT/mTOR pathway e.g. mTOR inhibitors, PI3K inhibitors, PDK1 inhibitors, AKT inhibitors or dual PI3K/mTOR inhibitors, inhibitors of the Ras/Raf/MEK/ERK pathway e.g. farnesyl transferase inhibitors or inhibitors of Ras (e.g. H-Ras, K-Ras, or N-Ras) or of Raf (A-Raf, B-Raf, or C-Raf) oncogenic or wild-type isoforms or MEK inhibitors, telomerase inhibitors, methionine aminopeptidase inhibitors, heparanase inhibitors, inhibitors of the Flt-3R receptor kinase family, inhibitors of the C-kit receptor kinase family, inhibitors of the RET receptor kinase family, inhibitors of the MET receptor kinase family, inhibitors of the RON receptor kinase family, inhibitors of the TEK/TIE receptor kinase family, CDK inhibitors, PLK inhibitors (e.g. PLK1 inhibitors), immunotherapeutics, radioimmunotherapeutics or (antiproliferative, pro-apoptotic or antiangiogenic) antibodies.

Histone deacetylase (HDAC) inhibitors may include, without being limited to, panobinostat (LBH-589), suberoylanilide hydroxamic acid (SAHA, vorinostat, Zolinza), depsipeptide (romidepsin), belinostat, resminostat, entinostat, mocetinostat, givinostat, and valproic acid.

Proteasome inhibitors may include, without being limited to, bortezomib (Velcade), and carfilzomib.

Heat shock protein 90 inhibitors may include, without being limited to, tanespimycin (17-AAG), geldamycin, retaspimycin (IPI-504), and AUY-922.

Ras-farnesyltransferase inhibitors are compounds that inhibit farnesyltransferase and Ras and may include, without being limited to, tipifarnib (Zarnesta) and lonafarnib.

Abl inhibitors may include, without being limited to, bosutinib (also inhibitor of Src), dasatinib (also inhibitor of Bcr and Src), imatinib (also inhibitor of Bcr), ponatinib (also inhibitor of Bcr and Src) and nilotinib (also inhibitor of Kit and PDGFR).

mTOR inhibitors may include, without being limited to, rapamycin (sirolimus, Rapamune) or rapalogues, everolimus (Certican, RAD-001), ridaforolimus (MK-8669, AP-23573, deforolimus), temsirolimus (Torisel, CCI-779), OSI-027, INK-128, AZD-2014, or AZD-8055 or [5-[2,4-bis[(3S)-3-methylmorpholin-4-yl]pyrido[5,6-e]pyrimidin-7-yl]-2-methoxyphenyl]methanol, and the like.

PI3K inhibitors may include, without being limited to, BKM-120, XL-147, RG-7321 (GDC-0941), CH-5132799 and BAY-80-6946. In an embodiment, a PI3K inhibitor within the meaning of this invention refers to an inhibitor of PI3K-alpha (such as e.g. BYL-719).

Dual PI3K/mTOR inhibitors may include, without being limited to, BEZ-235, XL-765, PF-4691502, GSK-2126458, RG-7422 (GDC-0980) and PKI-587.

Raf inhibitors may include, without being limited, sorafenib (Nexavar) or PLX-4032 (vemurafenib) or GSK-2118436 (dabrafenib). In an embodiment, a Raf inhibitor within the meaning of this invention refers to an inhibitor of BRaf (e.g. BRaf V600), particularly to a BRaf V600E inhibitor (such as e.g. PLX-4032 or GSK-2118436).

Deltoids and retinoids may include, without being limited to, all-trans retinoic acid (ATRA), fenretinide, tretinoin, bexarotene, and the like.

Toll-like receptor agonists may include, without being limited to, litenimod, agatolimod, and the like.

Antisense oligonucleotides may include, without being limited to, oblimersen (Genasense).

PLK inhibitors may include, without being limited to, the PLK1 inhibitor volasertib.

AKT inhibitors may include, without being limited to, MK-2206, or N-{(1S)-2-amino-1-[(3,4-difluorophenylmethyl]ethyl}-5-chloro-4-(4-chloro-1-methyl-1H-pyrazol-5-yl)-2-furancarboxamide.

MEK inhibitors other than the dual compounds according to this invention may include, without being limited to, selumetinib (AZD-6244), or N-[3-[3-cyclopropyl-5-[(2-fluoro-4-iodophenyl)amino]-3,4,6,7-tetrahydro-6,8-dimethyl-2,4,7-trioxopyrido[4,3-d]pyrimidin-1(2H)-yl]phenyl]acetamide (GSK-1120212).

Inhibitors within the meaning of this invention may include, without being limited to, small molecule inhibitors and antibodies.

Unless otherwise noted, kinase inhibitors mentioned herein may include single kinase inhibitors, which inhibit specifically one kinase and/or one kinase isoform, or multi-kinase inhibitors, which inhibit two or more kinases and/or two or more kinase isoforms (e.g. dual or triple kinase inhibitors or pan-kinase inhibitors).

The other anti-cancer agents as mentioned herein (particularly the small molecules among them) may also comprise any pharmaceutically acceptable salts thereof, hydrates and solvates thereof, including the respective crystalline forms.

By antibodies is meant, e.g., intact monoclonal antibodies (including, but not limited to, human, murine, chimeric and humanized monoclonal antibodies), polyclonal antibodies, conjugated (monoclonal) antibodies (e.g. those antibodies joined to a chemotherapy drug, radioactive particle, a cell toxin, or the like), multispecific antibodies formed from at least 2 intact antibodies, and antibodies fragments so long as they exhibit the desired biological activity.

Examples for antibodies which may be used within the combination therapy of this invention, may be anti-CD19 antibodies such as e.g. blinatumomab, anti-CD20 antibodies such as e.g. rituximab (Rituxan), veltuzumab, tositumumab, obinutuzumab or ofatumumab (Arzerra), anti-CD 22 antibodies such as e.g. epratuzumab, anti-CD23 antibodies such as e.g. lumiliximab, anti-CD30 antibodies such as e.g. iratumumab, anti-CD33 antibodies such as e.g. gemtuzumab or lintuzumab, anti-CD40 antibodies such as e.g. lucatumumab or dacetuzumab, anti-CD51 antibodies such as e.g. inetumumab, anti-CD52 antibodies such as e.g. alemtuzumab (Campath), anti-CD74 antibodies such as e.g. milatuzumab, anti-CD80 antibodies such as e.g. galiximab, anti-CTLA4 antibodies such as e.g. tremelimumab or ipilimumab, anti-TRAIL antibodies such as e.g. the anti-TRAIL1 antibodies mapatumumab or the anti-TRAIL2 antibodies tigatuzumab, conatumumab or lexatumumab, anti-Her2/neu antibodies such as e.g. trastuzumab (Herceptin), pertuzumab (Omnitarg) or ertumaxomab, anti-EGFR antibodies such as e.g. cetuximab (Erbitux), nimotuzumab, zalutumumab or panitumumab (Vectibix), anti-VEGF antibodies such as e.g. bevacizumab (Avastin), anti-VEGFR antibodies such as e.g. ramucirumab, anti-IGFR antibodies such as e.g. figitumumab, cixutumumab, dalotuzumab or robatumumab, or anti-HGFR antibodies such as e.g. rilotumumab, or conjugated antibodies such as e.g. the radiolabeled anti-CD20 antibodies ibritumomab tiuxetan (a $^{90}$Y-conjugate, Zevalin) or tositumomab (a $^{131}$I-conjugate, Bexxar), or the immunotoxins gemtuzumab ozogamicin (an anti-CD33 calicheamicin conjugate, Mylotarg), inotuzumab ozagamicin (an anti-CD22 calicheamicin conjugate), BL-22 (an anti-CD22 immunotoxin), brentuximab vedotin (an anti-CD30 auristatin E conjugate), or $^{90}$Y-epratuzumab (an anti-CD22 radioimmunoconjugate).

The therapy (mono- or combination therapy) according to this invention may also be combined with other therapies such as surgery, radiotherapy (e.g. irradiation treatment), radio-immunotherapy, endocrine therapy, biologic response modifiers, hyperthermia, cryotherapy and/or agents to attenuate any adverse effect, e.g. antiemetics.

In an embodiment, the therapeutic combination or (combined) treatment of this invention may further involve or comprise surgery and/or radiotherapy.

Accordingly, the present invention further provides a method of treating a cancer (e.g. selected from those described herein) in a human patient in need thereof which comprises the administration of a therapeutically effective amount of a dual Aurora kinase/MEK inhibitor of this invention, preferably selected from the group A consisting of the compounds 1 to 27 indicated herein above, or a tautomer or pharmaceutically acceptable salt thereof, and one or more other anti-cancer agents, preferably selected from those anti-cancer agents mentioned hereinbefore and hereinafter.

Further, the present invention further provides a combination which comprises a dual Aurora kinase/MEK inhibitor of this invention, preferably selected from the group A consisting of the compounds 1 to 27 indicated herein above, or a tautomer or pharmaceutically acceptable salt thereof, and one or more other anti-cancer agents, preferably selected from those anti-cancer agents mentioned hereinbefore and hereinafter.

In a certain embodiment, the combination therapy of this invention is used for the treatment of patients with pancreatic cancer, colorectal cancer, malignant melanoma, NSCLC or other advanced or metastatic solid tumors harboring KRAS, NRAS and/or BRAF (e.g. BRAF V600) mutations.

In a particular embodiment, the combination therapy of this invention is used for the treatment of patients with pancreatic cancer (PAC) harboring one or more mutations in KRAS or of wildtype genotype.

In a particular embodiment, the combination therapy of this invention is used for the treatment of patients with colorectal cancer (CRC) having one or more mutations in KRAS or in BRAF (e.g. BRAF V600).

In a particular embodiment, the combination therapy of this invention is used for the treatment of patients with malignant melanoma having one or more mutations in BRAF (particularly BRAF V600) or in NRAS.

In a particular embodiment, the combination therapy of this invention is used for the treatment of patients with non-small cell lung cancer (NSCLC) having one or more mutations in KRAS.

In an embodiment of this invention, the one or more other anti-cancer agents are selected from the group consisting of: capecitabine, 5-fluorouracil, oxaliplatin, cisplatin, carboplatin, dacarbazine, temozolamide, fotemustine, irinotecan, gemcitabine, pemetrexed, paclitaxel, docetaxel,
an angiogenesis inhibitor, a VEGF(R) inhibitor, an EGF(R) inhibitor, an IGF(R) inhibitor, an anti-CTLA4 antibody, a BRaf inhibitor, a mTOR inhibitor, a dual PI3K/mTOR inhibitor, a AKT inhibitor, and a PI3K inhibitor.

In an embodiment of this invention, the one or more other anti-cancer agents include an angiogenesis inhibitor. In a certain embodiment, the angiogenesis inhibitor is bevacizumab.

In an embodiment, the one or more other anti-cancer agents include a VEGF(R) inhibitor. In a certain embodiment, the VEGFR inhibitor is nintedanib.

In an embodiment, the one or more other anti-cancer agents include a EGF(R) inhibitor. In a certain embodiment, the EGFR inhibitor is afatinib. In another certain embodiment, the EGFR inhibitor is selected from cetuximab, panitumumab and erlotinib.

In an embodiment, the one or more other anti-cancer agents include a IGF(R) inhibitor. In a certain embodiment, the IGF(R) inhibitor is selected from figitumumab, dalotuzumab, cixutumumab, ganitumab, BMS-754807 and OSI-906 (linsitinib).

In an embodiment, the one or more other anti-cancer agents include an anti-CTLA4 antibody. In a certain embodiment, the anti-CTLA4 antibody is ipilimumab.

In an embodiment, the one or more other anti-cancer agents include a BRaf inhibitor. In a certain embodiment the BRaf inhibitor is PLX-4032 (vemurafenib). In another certain embodiment the BRaf inhibitor is GSK-2118436 (dabrafenib).

In an embodiment, the one or more other anti-cancer agents include a BRaf inhibitor (such as e.g. dabrafenib or vemurafenib) optionally in combination with a MEK inhibitor (such as e.g. selumetinib or GSK-1120212) other than the dual Aurora kinase/MEK inhibitor of this invention.

In an embodiment, the one or more other anti-cancer agents includes a mTOR inhibitor. In a certain embodiment the mTOR inhibitor is (5-{2,4-bis[(3S)-3-methylmorpholin-4-yl]pyrido[2,3-d]pyrimidin-7-yl}-2-methoxyphenyl)methanol (AZD-8055).

In an embodiment, the one or more other anti-cancer agents includes a dual PI3K/mTOR inhibitor. In a certain embodiment the dual PI3K/mTOR inhibitor is 2-methyl-2-[4-(3-methyl-2-oxo-8-quinolin-3-yl-2,3-dihydro-imidazo[4,5-c]quinolin-1-yl)-phenyl]-propionitrile (BEZ-235).

In an embodiment, the one or more other anti-cancer agents includes a PI3K inhibitor. In a certain embodiment the PI3K inhibitor is 5-[2,6-di(4-morpholinyl)-4-pyrimidinyl]-4-(trifluoromethyl)-2-pyridinamine (BKM-120).

In an embodiment, the one or more other anti-cancer agents includes a AKT inhibitor. In a certain embodiment the AKT inhibitor is 8-[4-(1-aminocyclobutyl)phenyl]-9-phenyl-1,2,4-triazolo[3,4-f][1,6]naphthyridin-3(2H)-one (MK-2206). In another certain embodiment the AKT inhibitor is N-{(1S)-2-amino-1-[(3,4-difluorophenyl)methyl]ethyl}-5-chloro-4-(4-chloro-1-methyl-1H-pyrazol-5-yl)-2-furancarboxamide.

In an embodiment of this invention, the one or more other anti-cancer agents are selected from the group consisting of: capecitabine, 5-fluorouracil, oxaliplatin, cisplatin, carboplatin, dacarbazine, temozolamide, fotemustine, irinotecan, gemcitabine, pemetrexed, paclitaxel, docetaxel, bevacizumab, cetuximab, panitumumab, erlotinib, ipilimumab, figitumumab, dalotuzumab, cixutumumab, ganitumab, BMS-754807, OSI-906 (linsitinib), PLX-4032 (vemurafenib), GSK-2118436 (dabrafenib), AZD-8055, BEZ-235, BKM-120, MK-2206, afatinib, and nintedanib.

In a further embodiment (embodiment E1), the one or more other anti-cancer agents according to this invention is/are selected from the group (group G1) consisting of capecitabine, 5-fluorouracil, oxaliplatin, cisplatin, carboplatin, dacarbazine, temozolamide, fotemustine, irinotecan, gemcitabine, pemetrexed, paclitaxel and docetaxel.

In a further embodiment (embodiment E2), the one or more other anti-cancer agents according to this invention is/are selected from the group (group G2) consisting of bevacizumab, cetuximab, panitumumab, erlotinib and ipilimumab.

In a further embodiment (embodiment E3), the one or more other anti-cancer agents according to this invention is/are selected from the group (group G3) consisting of figitumumab, dalotuzumab, cixutumumab, ganitumab, BMS-754807, OSI-906 (linsitinib), PLX-4032 (vemurafenib), GSK-2118436 (dabrafenib), AZD-8055, BEZ-235, BKM-120, MK-2206, afatinib and nintedanib.

For example, it can be found that by using a dual Aurora kinase/MEK inhibitor of this invention in combination with an agent targeting (e.g. inhibiting) the IGF/PI3K/AKT/mTOR axis an improvement in antitumoral response, such as e.g. inhibition or prevention of cell cycle progression, supression of cell proliferation, regulation of cell growth, inhibition of DNA synthesis or inducement of apoptosis, can be achieved in patients in need thereof (such as e.g. in those patients described herein). Further, the combination of a dual Aurora kinase/MEK inhibitor of this invention and an inhibitor in the IGF/PI3K/AKT axis may also block the compensatory feedback loop induced by MEK inhibition.

For further example, it can be found that by using a dual Aurora kinase/MEK inhibitor of this invention in combination with a BRaf inhibitor an improvement in anticancer effect or antitumoral response, such as e.g. blocking cell proliferation and stronger pathway inhibition which may result in cytotoxic effect as opposed to cytostatic effect, can be achieved in patients in need thereof (such as e.g. in those patients described herein). Further, the combination of a dual Aurora kinase/MEK inhibitor and a BRaf inhibitor may be also used for delaying the onset, overcoming, treating or preventing drug resistance to either of them particularly in RAS or BRaf mutant tumors (e.g. advanced solid tumors harboring RAS or BRAF V600 mutations, such as those described herein).

For further example, it can be found that by using a dual Aurora kinase/MEK inhibitor of this invention in combination with a mTOR inhibitor an improvement in anticancer effect or antitumoral response, such as e.g. supression of cell proliferation, regulation of cell growth, or inhibition/slowing of cell protein translation, can be found in patients in need thereof (such as e.g. in those patients described herein).

For further example, it can be found that by using a dual Aurora kinase/MEK inhibitor of this invention in combination with an EGF(R) inhibitor an improvement in anticancer effect or antitumoral response, such as e.g. supression of cell proliferation, enhancement of cytotoxicity e.g. in tumors with or without EGFR mutations, or regulation of tumor growth or size, increased tumor regression or decreased metastasis, can be found in patients in need thereof (such as e.g. in those patients described herein). Further, the combination of a dual Aurora kinase/MEK inhibitor and an EGF(R) inhibitor may be also used for delaying the onset, overcoming, treating or preventing drug resistance to either of them.

For further example, it can be found that by using a dual Aurora kinase/MEK inhibitor of this invention in combination with an angiogenesis inhibitor (e.g. a VEGF(R) inhibitor) an improvement in anticancer effect or antitumoral response, such as e.g. inhibiting or slowing tumor growth, can be found in patients in need thereof (such as e.g. in those patients described herein).

For further example, it can be found that by using a dual Aurora kinase/MEK inhibitor of this invention in combination with a (standard) chemotherapeutic anti-cancer agent an improvement in anticancer effect or antitumoral response, such as e.g. enhancement of cytotoxicity while lowering the prescriped dose of the (standard) chemotherapeutic drug necessary for effective treatment or prevention or delay of onset of drug resistance to either of them, can be found in patients in need thereof (such as e.g. in those patients described herein).

Anti-cancer effects of a method of treatment or of a therapeutic use of the present invention include, but are not limited to, anti-tumor effects, the response rate (e.g. overall response rate), the time to disease progression or the survival rate (e.g. progression free survival or overall survival). Anti-tumor effects of a method of treatment of the present invention include but are not limited to, inhibition of tumor growth, tumor growth delay, regression of tumor, shrinkage of tumor, increased time to regrowth of tumor on cessation of treatment, slowing of disease progression.

It is expected that when a method of treatment or therapeutic use of the present invention is administered to a warm-blooded animal such as a human, in need of treatment for cancer, said method of treatment will produce an effect, as measured by, for example, one or more of: the extent of the anti-tumor effect, the response rate, the time to disease progression and the survival rate. Anti-cancer effects may include prophylactic treatment as well as treatment of existing disease.

Further, the combinations according to this invention may help overcome resistance to either treatment in monotherapy.

In a particular embodiment (embodiment F1) within combination therapy of this invention, the combinations, compositions, methods and uses according to this invention relate to combinations comprising a dual Aurora kinase/MEK and an other anti-cancer agent, wherein the dual Aurora kinase/MEK inhibitor of this invention is selected from the group A consisting of the compounds 1 to 27 indicated herein above and the other anti-cancer agent is preferably selected according to the entries in the following Table i.

TABLE i

| Sub-Embodiment | other anti-cancer agent |
| --- | --- |
| F1.1 | an angiogenesis inhibitor |
| F1.2 | a VEGF(R) inhibitor |
| F1.3 | bevacizumab |
| F1.4 | nintedanib |
| F1.5 | an EGF(R) inhibitor |

TABLE i-continued

| Sub-Embodiment | other anti-cancer agent |
| --- | --- |
| F1.6 | cetuximab |
| F1.7 | panitumumab |
| F1.8 | erlotinib |
| F1.9 | afatinib |
| F1.10 | an anti-CTLA4 antibody |
| F1.11 | ipilimumab |
| F1.12 | an IGF(R) inhibitor |
| F1.13 | figitumumab |
| F1.14 | dalotuzumab |
| F1.15 | cixutumumab |
| F1.16 | ganitumab |
| F1.17 | linsitinib |
| F1.18 | BMS-754807 |
| F1.19 | a BRaf selective inhibitor |
| F1.20 | vemurafenib |
| F1.21 | dabrafenib |
| F1.22 | a mTOR inhibitor |
| F1.23 | AZD-8055 |
| F1.24 | a dual PI3K/mTOR inhibitor |
| F1.25 | BEZ-235 |
| F1.26 | a PI3K inhibitor |
| F1.27 | BKM-120 |
| F1.28 | an AKT inhibitor |
| F1.29 | MK-2206 |
| F1.30 | capecitabine |
| F1.31 | 5-fluorouracil |
| F1.32 | oxaliplatin |
| F1.33 | cisplatin |
| F1.34 | carboplatin |
| F1.35 | dacarbazine |
| F1.36 | temozolamide |
| F1.37 | fotemustine |
| F1.38 | irinotecan |
| F1.39 | gemcitabine |
| F1.40 | pemetrexed |
| F1.41 | paclitaxel |
| F1.42 | docetaxel |

In some embodiments, for use in therapy of colorectal cancer (CRC) according to this invention, the dual Aurora kinase/MEK inhibitor may be combined with one or more other anti-cancer agents, such as e.g. selected from DNA replication inhibitors (such as e.g. oxaliplatin), topoisomerase I inhibitors (such as e.g. irinotecan), (oral) fluoropyrimidines (such as e.g. capecitabine), anti-angiogenic agents (such as e.g. bevacizumab), and/or EGFR inhibitors (such as e.g. anti-EGFR antibodies such as cetuximab or panitumumab), or combinations thereof.

In some embodiments, for use in therapy of pancreatic cancer (PAC) according to this invention, the dual Aurora kinase/MEK inhibitor may be combined with one or more other anti-cancer agents, such as e.g. selected from gemcitabine, DNA replication inhibitors (such as e.g. oxaliplatin, cisplatin), topoisomerase I inhibitors (such as e.g. irinotecan), fluoropyrimidines (such as e.g. 5-FU or capecitabine), anti-angiogenic agents (such as e.g. bevacizumab), and/or EGFR inhibitors (such as e.g. cetuximab or erlotinib), or combinations thereof.

In some embodiments, for use in therapy of melanoma according to this invention, the dual Aurora kinase/MEK inhibitor may be combined with one or more other anti-cancer agents, such as e.g. selected from dacarbazine, temozolomide, ipilimumab and/or BRaf inhibitors (such as e.g. vemurafenib), or combinations thereof.

For example, the following cancer diseases may be treated with compounds or combinations according to the invention, without, however, being restricted thereto: brain tumours, such as acoustic neurinoma, astrocytomas such as piloid astrocytomas, fibrillary astrocytoma, protoplasmic astrocytoma, gemistocytic astrocytoma, anaplastic astrocytoma and glioblastomas, brain lymphomas, brain metastases, hypophyseal tumour such as prolactinoma, HGH (human growth hormone) producing tumour and ACTH-producing tumour (adrenocorticotrophic hormone), craniopharyngiomas, medulloblastomas, meningiomas and oligodendrogliomas; nerve tumours (neoplasms) such as tumours of the vegetative nervous system such as neuroblastoma sympathicum, ganglioneuroma, paraganglioma (phaeochromocytoma and chromaffinoma) and glomus caroticum tumour, tumours in the peripheral nervous system such as amputation neuroma, neurofibroma, neurinoma (neurilemoma, schwannoma) and malignant schwannoma, as well as tumours in the central nervous system such as brain and spinal cord tumours; intestinal cancer such as rectal carcinoma, colon carcinoma, anal carcinoma, small intestine tumours and duodenal tumours; eyelid tumours such as basalioma or basal cell carcinoma; pancreatic gland cancer or pancreatic carcinoma; bladder cancer or bladder carcinoma; lung cancer (bronchial carcinoma) such as small-cell bronchial carcinomas (oat cell carcinomas) and non-small-cell bronchial carcinomas such as squamous epithelium carcinomas, adenocarcinomas and large-cell bronchial carcinomas; breast cancer such as mammary carcinoma, such as infiltrating ductal carcinoma, colloid carcinoma, lobular invasive carcinoma, tubular carcinoma, adenoid cystic carcinoma, and papillary carcinoma; non-Hodgkin's lymphomas (NHL) such as Burkitt's lymphoma, low-malignancy non-Hodkgin's lymphomas (NHL) and mucosis fungoides; uterine cancer or endometrial carcinoma or corpus carcinoma; CUP syndrome (cancer of unknown primary); ovarian cancer or ovarian carcinoma such as mucinous, endometrial or serous cancer; gall bladder cancer; bile duct cancer such as Klatskin's tumour; testicular cancer such as seminomas and non-seminomas; lymphoma (lymphosarcoma) such as malignant lymphoma, Hodgkin's disease, non-Hodgkin's lymphomas (NHL) such as chronic lymphatic leukaemia, hair cell leukaemia, immunocytoma, plasmocytoma (multiple myeloma), immunoblastoma, Burkitt's lymphoma, T-zone mycosis fungoides, large-cell anaplastic lymphoblastoma and lymphoblastoma; laryngeal cancer such as vocal cord tumours, supraglottal, glottal and subglottal laryngeal tumours; bone cancer such as osteochondroma, chondroma, chrondoblastoma, chondromyxoidfibroma, osteoma, osteoid-osteoma, osteoblastoma, eosinophilic granuloma, giant cell tumour, chondrosarcoma, osteosarcoma, Ewing's sarcoma, reticulosarcoma, plasmocytoma, fibrous dysplasia, juvenile bone cyst and aneurysmatic bone cyst; head/neck tumours such as tumours of the lips, tongue, floor of the mouth, oral cavity, gingiva, pallet, salivary glands, pharynx, nasal cavities, paranasal sinuses, larynx and middle ear; liver cancer such as liver cell carcinoma or hepatocellular carcinoma (HCC); leukaemias, such as acute leukaemias, such as acute lymphatic/lymphoblastic leukaemia (ALL), acute myeloid leukaemia (AML); chronic leukaemias such as chronic lymphatic leukaemia (CLL), chronic myeloid leukaemia (CML); stomach cancer or stomach carcinoma such as papillary, tubular and mucinous adenocarcinoma, signet ring cell carcinoma, adenoid squamous cell carcinoma, small-cell carcinoma and undifferentiated carcinoma; melanomas such as superficially spreading, nodular malignant lentigo and acral lentiginous melanoma; renal cancer, such as kidney cell carcinoma or hypernephroma or Grawitz's tumour; oesophageal cancer or oesophageal carcinoma; cancer of the penis; prostate cancer; pharyngeal cancer or pharyngeal carcinomas such as nasopharyngeal carcinomas, oropharyngeal carcinomas and hypopharyngeal carcinomas; retinoblastoma; vaginal cancer or vaginal carcinoma; squamous epithelium carcinomas, adeno carcinomas, in situ carcinomas, malignant melanomas and sarcomas; thyroid gland carcinomas such as papillary, follicular and medullary thyroid gland carcinoma, and also anaplastic carcinomas; spinalioma, prickle cell carcinoma and squamous epithelium carcinoma of the skin; thymomas, urethral cancer and vulvar cancer.

The therapeutic applicability of the dual Aurora kinase/MEK inhibitors or combinations according to this invention may include first line, second line, third line or further lines treatment of patients. The cancer may be metastatic, recurrent, relapsed, resistant or refractory to one or more anti-cancer treatments. Thus, the patients may be treatment naïve, or may have received one or more previous anti-cancer therapies, which have not completely cured the disease.

Patients with relapse and/or with resistance or failure to one or more other (standard) anti-cancer agents are also amenable for treatment with a dual Aurora kinase/MEK inhibitor of this invention, e.g. for second or third line treatment cycles, optionally in combination with one or more other anti-cancer agents (e.g. as add-on combination or as replacement treatment).

Accordingly, some of the disclosed methods involving a dual Aurora kinase/MEK inhibitor of this invention are effective at treating subjects whose cancer has relapsed, or whose cancer has become drug resistant or multi-drug resistant, or whose cancer has failed one, two or more lines of (mono- or combination) therapy with one or more other anti-cancer agents (e.g. with one or more other anti-cancer agents as mentioned herein, particularly standard chemotherapeutic, targeted or non-targeted drugs).

A cancer which initially responded to an anti-cancer drug (such as e.g. an anti-cancer agent as described herein) can relapse and it becomes resistant to the anti-cancer drug when the anti-cancer drug is no longer effective in treating the subject with the cancer, e.g. despite the administration of increased dosages of the anti-cancer drug. Cancers that have developed resistance to two or more anti-cancer drugs are said to be multi-drug resistant.

Accordingly, in some methods of (combination) treatment of this invention, treatment with an agent (e.g. a dual Aurora kinase/MEK inhibitor) administered secondly or thirdly is begun if the patient has resistance or develops resistance to one or more agents administered initially or previously. The patient may receive only a single course of treatment with each agent or multiple courses with one, two or more agents.

In certain instances, combination therapy according to this invention may hence include initial or add-on combination, replacement or maintenance treatment.

Pharmaceutical compositions containing the active substance(s), and optionally one or more pharmaceutically acceptable carriers, excipients and/or diluents, may be prepared according to methods customary per se for the skilled person, or analogously or similarly to known procedures. A method for preparing such pharmaceutical composition according to this invention may comprise combining or mixing the active substance(s) and one or more pharmaceutically acceptable carriers, excipients and/or diluents.

Suitable preparations include for example tablets, capsules, suppositories, solutions,—e.g. solutions for injection (s.c., i.v., i.m.) and infusion—elixirs, emulsions or dispersible powders. The content of the pharmaceutically active compound(s) should be in the range from 0.1 to 90 wt.-%, preferably 0.5 to 50 wt.-% of the composition as a whole, i.e. in amounts which are sufficient to achieve the dosage range specified below. The doses specified may, if necessary, be given several times a day.

Suitable tablets may be obtained, for example, by mixing the active substances, optionally in combination, with known excipients, for example inert diluents such as calcium carbonate, calcium phosphate, cellulose or lactose, disintegrants such as corn starch or alginic acid or crospovidon, binders such as starch (e.g. pregelatinized starch), cellulose (e.g. microcrystalline cellulose), copovidone or gelatine, glidants, lubricants such as magnesium stearate or talc and/or agents for delaying release, such as carboxymethyl cellulose, cellulose acetate phthalate, or polyvinyl acetate. The tablets may be prepared by usual processes, such as e.g. by direct compression or roller compaction. The tablets may also comprise several layers.

For example, a suitable pharmaceutical composition (particularly solid oral dosage form, e.g. tablet) according to this invention comprises a dual Aurora kinase/MEK inhibitor of this invention and optionally one or more pharmaceutically acceptable carriers, excipients and/or diluents typically selected from lactose, microcrystalline cellulose, pregelatinized starch, copovidone, crospovidon, silicon dioxide and magnesium stearate.

Coated tablets may be prepared accordingly by coating cores produced analogously to the tablets with substances normally used for tablet coatings (e.g. polymer or polysaccharide based, optionally with plasticizers and pigments included), for example collidone or shellac, gum arabic, talc, titanium dioxide or sugar. To achieve delayed release or prevent incompatibilities the core may also consist of a number of layers. Similarly the tablet coating may consist of a number of layers to achieve delayed release, possibly using the excipients mentioned above for the tablets.

For example, a suitable coated tablet according to this invention includes a film-coat comprising a film-forming agent, a plasticizer, a glidant and optionally one or more pigments.

Syrups or elixirs containing the active substances or combinations thereof according to the invention may additionally contain a sweetener such as saccharine, cyclamate, glycerol or sugar and a flavour enhancer, e.g. a flavouring such as vanillin or orange extract. They may also contain suspension adjuvants or thickeners such as sodium carboxymethyl cellulose, wetting agents such as, for example, condensation products of fatty alcohols with ethylene oxide, or preservatives such as p-hydroxybenzoates.

Solutions for injection and infusion are prepared in the usual way, e.g. with the addition of isotonic agents, preservatives such as p-hydroxybenzoates, or stabilisers such as alkali metal salts of ethylenediamine tetraacetic acid, optionally using emulsifiers and/or dispersants, whilst if water is used as the diluent, for example, organic solvents may optionally be used as solvating agents or dissolving aids, and transferred into injection vials or ampoules or infusion bottles.

Capsules containing one or more active substances or combinations of active substances may for example be prepared by mixing the active substances with inert carriers such as lactose or sorbitol and packing them into gelatine capsules.

Suitable suppositories may be made for example by mixing with carriers provided for this purpose, such as neutral fats or polyethyleneglycol or the derivatives thereof.

Excipients which may be used include, for example, water, pharmaceutically acceptable organic solvents such as paraffins (e.g. petroleum fractions), vegetable oils (e.g. groundnut or sesame oil), mono- or polyfunctional alcohols (e.g. ethanol or glycerol), carriers such as e.g. natural mineral powders (e.g. kaolins, clays, talc, chalk), synthetic mineral powders (e.g. highly dispersed silicic acid and silicates), sugars (e.g. cane sugar, lactose and glucose) emulsifiers (e.g. lignin, spent sulphite liquors, methylcellulose, starch and polyvinylpyrrolidone) and lubricants (e.g. magnesium stearate, talc, stearic acid and sodium lauryl sulphate).

The elements of the combinations of this invention may be administered (optionally independently) by methods customary to the skilled person, e.g. by oral, enterical, parenteral (e.g., intramuscular, intraperitoneal, intravenous, transdermal or subcutaneous injection, or implant), nasal, vaginal, rectal, or topical routes of administration and may be formulated, alone or together, in suitable dosage unit formulations containing conventional non-toxic pharmaceutically acceptable carriers, adjuvants and vehicles appropriate for each route of administration.

The dual Aurora kinase/MEK inhibitors of this invention are administered by the usual methods, preferably by oral or parenteral route, most preferably by oral route. For oral administration the tablets may contain, apart from the above-mentioned carriers, additives such as sodium citrate, calcium carbonate and dicalcium phosphate together with various additives such as starch, preferably potato starch, gelatine and the like. Moreover, glidants and/or lubricants such as magnesium stearate, sodium lauryl sulphate and talc may be used at the same time for the tabletting process. In the case of aqueous suspensions the active substances may be combined with various flavour enhancers or colourings in addition to the excipients mentioned above.

For parenteral use, solutions of the active substances with suitable liquid carriers may be used.

The dosage for oral use is from 1-2000 mg per day (e.g. from 50 to 700 mg per day). The dosage for intravenous use is from 1-1000 mg per hour, preferably between 5 and 500 mg per hour.

However, it may sometimes be necessary to depart from the amounts specified, depending on the body weight, the route of administration, the individual response to the drug, the nature of its formulation and the time or interval over which the drug is administered. Thus, in some cases it may be sufficient to use less than the minimum dose given above, whereas in other cases the upper limit may have to be exceeded. When administering large amounts it may be advisable to divide them up into a number of smaller doses spread over the day.

The present invention is not to be limited in scope by the specific embodiments described herein. Various modifications of the invention in addition to those described herein may become apparent to those skilled in the art from the present disclosure. Such modifications are intended to fall within the scope of the appended claims.

All patent applications cited herein are hereby incorporated by reference in their entireties.

Further embodiments, features and advantages of the present invention may become apparent from the following examples. The following examples serve to illustrate, by way of example, the principles of the invention without restricting it.

EXAMPLES

1. Aurora B Kinase Assays:
Radioactive Kinase Assay Using a Wild Type (wt)-*Xenopus laevis* Aurora B/INCENP Complex:

Protein Expression: Preparation of the wild type (wt)-*Xenopus laevis* Aurora $B^{60-361}$/INCENP$^{790-847}$ complex was performed essentially as described in Sessa et al. 2005.

The ATP-$K_M$ value of the complex is 61 µM. The kinase assays are run in the presence of 100 µM ATP using 10 µM of a substrate peptide. pAUB-IN847 was used to transform the

*E. coli* strain BL21(DE3) containing the pUBS520 helper plasmid. Both proteins and their mutants are expressed and purified under essentially identical conditions. Protein expression is induced with 0.3 mM IPTG at an $OD_{600}$ of 0.45-0.7. Expression is then continued for about 12-16 hours at 23-25° C. with agitation. Bacterial cells are harvested by centrifugation at 4000 rpm×15 min in a Beckman JLA 8.1 rotor, and the pellets resuspended in lysis buffer (50 mM Tris HCl pH 7.6, 300 mM NaCl, 1 mM DTT, 1 mM EDTA, 5% glycerol, Roche Complete protease inhibitor tablets). 20-30 ml lysis buffer are used per liter of *E. coli* culture. Cells are lysed by sonication, and the lysates cleared by centrifugation at 12000 rpm for 45-60 min on a JA20 rotor. The supernatants are incubated with 300 µl of GST Sepharose Fast Flow (Amersham Biosciences) per liter of bacterial culture. The resin is first washed with PBS buffer and finally equilibrated with lysis buffer. After a 4-5 hour agitation at 4° C., the beads are washed with 30 volumes of lysis buffer, and then equilibrated with 30 volumes of cleavage buffer (50 mM Tris pH 7.6, 150 mM NaCl, 1 mM DTT, 1 mM EDTA). To cleave the GST from Aurora B, 10 units of Prescission protease (Amersham Biosciences) per milligram of substrate are added and the incubation is protracted for 16 hours at 4° C. The supernatant, which contains the cleaved product, is collected and loaded onto a 6 ml Resource Q column (Amersham Biosciences) equilibrated with Ion Exchange buffer (50 mM Tris pH 7.6, 150 mM NaCl, 1 mM DTT, 1 mM EDTA). The Aurora B/INCENP complex is collected in the flow through of the column. The flow-through of the Resource Q column is concentrated and loaded onto a Superdex 200 size-exclusion chromatography (SEC) column equilibrated with SEC buffer (Tris HCl 10 mM pH 7.6, NaCl 150 mM, DTT 1 mM, EDTA 1 mM). Fractions containing Aurora-B/INCENP are collected and concentrated using Vivaspin concentrators (MW cutoff 3-5K) to a final concentration of 12 mg/ml. The final yield is about 1-2 mg of pure complex per liter of bacteria. Purified (wt)-*Xenopus laevis* Aurora $B^{60-361}$/$INCENP^{790-847}$ complex was stored at −80° C. in desalting buffer (50 mM Tris/Cl pH 8.0, 150 mM NaCl, 0.1 mM EDTA, 0.03% Brij-35, 10% glycerol, 1 mM DTT).

Assay Conditions: Enzyme activity was assayed in the presence or absence of serial inhibitor dilutions. For the kinase assay (reaction volume 50 µl/well), 96-well PP-Microplates (Greiner, 655 201) were used. To 10 µl compound in 25% DMSO were added: 30 µl PROTEIN-MIX (166 µM ATP, kinase buffer [50 mM Tris/HCl pH 7.5, 25 mM $MgCl_2$, 25 mM NaCl], 10 ng wt-Aurora-B60-361/INCENP790-847) followed by an 15 min incubation at room temperature (agitating, 350 rpm). To this, 10 µl PEPTIDE-MIX (2× kinase buffer, 5 mM NaF, 5 mM DTT, 1 µCi $^{33}$P-ATP, 50 µM peptide (Biotin-LRRSLGLRRSLGLRRW SLGLRRSLG) was added. The mixture was incubated for 60 min at room temperature (agitating, 350 rpm), followed by addition of 180 µl 6.4% TCA (final concentration: 5%) to stop the reaction. Subsequently, a Multiscreen filtration plate (Millipore, MAIP N0B 10) was equilibrated with 100 µl 70% ethanol and 1% TCA prior to addition of the stopped kinase reaction. Following 5 washes with 180 µl 1% TCA, the lower part of the plate was dried. 25 µl scintillation cocktail (Microscint, High Efficiency LSC-Cocktail, Packard, 6013611) was added and the incorporated gamma phosphate was measured in a suitable scintillation counter.

Data Analysis: Inhibitor concentrations were transformed to logarithmic values and the raw data were normalized. These normalized values were used to calculate the $IC_{50}$ values. Data was fitted by iterative calculation using a sigmoidal curve analysis program (Graph Pad Prism version 3.0) with variable Hill slope. Each microtiter plate contained internal controls, such as blank, maximum reaction and historical reference compound.

Analysis of Histone H3 Phosphorylation in NCI-H460 Cells:

NCI-H460 cells were plated in 96 well flat bottom Falcon plates at a cell density of 4000 cells/well. On the next day, cells were synchronized by treating them for 16 hrs with 300 nM BIVC0030BS. This CDK1 inhibitor arrests cells in G2. The cells were released from the inhibitory G2 block by washing once with medium. The synchronous entry into mitosis results in a high percentage (70-80%) of mitotic cells after 60 min. Fresh medium and compounds were added to the wells, each drug concentration in duplicates. The final volume per well was 200 µl and the final concentration of the test compounds covered the range between 10 µM and 5 nM. The final DMSO concentration was 0.1%. Cells were incubated at 37° C. and 5% $CO_2$ in a humidified atmosphere for exactly 60 minutes. The medium was aspirated and the cells were fixed and permeabilized with 100 µl warm 4% formaldehyde solution containing Triton X-100 (1:200) for 10 min at RT. After washing twice with blocking buffer (0.3% BSA/PBS), 50 µl solution of polyclonal antibody anti-phospho H3 (Ser28) diluted 1:500 was added for 1 hr at RT. After washing twice with blocking buffer, cells were incubated with 50 µl goat-anti rabbit F(ab)$_2$ fragment Alexa Fluor 594 (1:2000)+DAPI (final concentration 300 nM) for 1 hr at RT in the dark. The plates were washed, 200 µl PBS were added, the plates sealed with black foil and analyzed in a Cellomics ArrayScan applying the Cell Cycle BioApplication program. The data generated in the assay were analyzed by the program PRISM (GraphPad Inc.). The inhibitor concentrations were transformed to logarithmic values and $EC_{50}$ was calculated by a nonlinear regression curve fit (sigmoidal dose-response (variable slope)).

2. MEK Kinase Assays:

MEK inhibitory activity of a compound is measured using the Z'-LYTE™ kinase assay of Invitrogen.

The Z'-LYTE® biochemical assay employs a fluorescence-based, coupled-enzyme format and is based on the differential sensitivity of phosphorylated and non-phosphorylated peptides to proteolytic cleavage. The peptide substrate is labeled with two fluorophores—one at each end—that make up a FRET pair.

In the primary reaction, the kinase transfers the gamma-phosphate of ATP to a single tyrosine, serine or threonine residue in a synthetic FRET-peptide. In the secondary reaction, a site-specific protease recognizes and cleaves non-phosphorylated FRET-peptides. Phosphorylation of FRET-peptides suppresses cleavage by the Development Reagent. Cleavage disrupts FRET between the donor (i.e. coumarin) and acceptor (i.e., fluorescein) fluorophores on the FRET-peptide, whereas uncleaved, phosphorylated FRET-peptides maintain FRET. A ratiometric method, which calculates the ratio (the Emission Ratio) of donor emission to acceptor emission after excitation of the donor fluorophore at 400 nm, is used to quantitate reaction progress, as shown in the equation as follows:

$$\text{Emission Ratio} = \text{Coumarin emission (445 nM)}/\text{Fluorescein Emission (520 nM)}.$$

Both cleaved and uncleaved FRET-peptides contribute to the fluorescence signals and therefore to the Emission Ratio. The extent of phosphorylation of the FRET-peptide can be calculated from the Emission Ratio. The Emission Ratio will remain low if the FRET-peptide is phosphorylated (i.e., no kinase inhibition) and will be high if the FRET-peptide is non-phosphorylated (i.e., kinase inhibition).

The Test Compounds are screened in 1% DMSO (final) in the well. For 10 point titrations, 3-fold serial dilutions are conducted from the starting concentration (1 µM).

All Peptide/Kinase Mixtures are diluted to a 2× working concentration in the appropriate Kinase Buffer.

All ATP Solutions are diluted to a 4× working concentration in Kinase Buffer (50 mM HEPES pH 7.5, 0.01% BRIJ-35, 10 mM MgCl2, 1 mM EGTA).

ATP Km apparent is previously determined using a T-LYTE® assay.

Assay Protocol:
1. 2.5 µL—4× Test Compound or 100 nL 100× plus 2.4 µL kinase buffer
2. 5 µL—2× Peptide/Kinase Mixture
3. 2.5 µL—4×ATP Solution
4. 30-second plate shake
5. 60-minute Kinase Reaction incubation at room temperature
6. 5 µL—Development Reagent Solution
7. 30-second plate shake
8. 60-minute Development Reaction incubation at room temperature
9. Read on fluorescence plate reader and analyze the data MAP2K1 (MEK1) Specific Assay Conditions—Cascade Format:

The 2×MAP2K1 (MEK1)/inactive MAPK1 (ERK2)/Ser/Thr 03 mixture is prepared in 50 mM HEPES pH 7.5, 0.01% BRIJ-35, 10 mM MgCl2, 1 mM EGTA. The final 10 µL Kinase Reaction consists of 1.29-5.18 ng MAP2K1 (MEK1), 105 ng inactive MAPK1 (ERK2), and 2 µM Ser/Thr 03 in 50 mM HEPES pH 7.5, 0.01% BRIJ-35, 10 mM MgCl2, 1 mM EGTA. After the 1 hour Kinase Reaction incubation, 5 µL of a 1:1024 dilution of Development Reagent A is added.

MAP2K2 (MEK2) Specific Assay Conditions—Cascade Format:

The 2×MAP2K2 (MEK2)/inactive MAPK1 (ERK2)/Ser/Thr 03 mixture is prepared in 50 mM HEPES pH 7.5, 0.01% BRIJ-35, 10 mM MgCl2, 1 mM EGTA. The final 10 µL Kinase Reaction consists of 1.13-4.5 ng MAP2K2 (MEK2), 105 ng inactive MAPK1 (ERK2), and 2 µM Ser/Thr 03 in 50 mM HEPES pH 7.5, 0.01% BRIJ-35, 10 mM MgCl2, 1 mM EGTA. After the 1 hour Kinase Reaction incubation, 5 µL of a 1:1024 dilution of Development Reagent A is added.

Z'-LYTE® Assay Controls:

0% Phosphorylation Control (100% Inhibition Control):

The maximum Emission Ratio is established by the 0% Phosphorylation Control (100% Inhibition Control), which contains no ATP and therefore exhibits no kinase activity. This control yields 100% cleaved peptide in the Development Reaction.

100% Phosphorylation Control:

The 100% Phosphorylation Control, which consists of a synthetically phosphorylated peptide of the same sequence as the peptide substrate, is designed to allow for the calculation of percent phosphorylation.

This control yields a very low percentage of cleaved peptide in the Development Reaction. The 0% Phosphorylation and 100% Phosphorylation Controls allow one to calculate the percent Phosphorylation achieved in a specific reaction well. Control wells do not include any kinase inhibitors.

0% Inhibition Control:

The minimum Emission Ratio in a screen is established by the 0% Inhibition Control, which contains active kinase. This control is designed to produce a 10-70% phosphorylated peptide in the Kinase Reaction.

A known inhibitor (staurosporine IC50 MEK1/MEK2 14.7 nM/15.2 nM at 100 µM ATP) control standard curve, 10 point titration, is run for each individual kinase on the same plate as the kinase to ensure the kinase is inhibited within an expected $IC_{50}$ range previously determined.

Development Reaction Interference:

The Development Reaction Interference is established by comparing the Test Compound Control wells that do not contain ATP versus the 0% Phosphorylation Control (which does not contain the Test Compound). The expected value for a non-interfering compound should be 100%. Any value outside of 90% to 110% is flagged.

Test Compound Fluorescence Interference:

The Test Compound Fluorescence Interference is determined by comparing the Test Compound Control wells that do not contain the Kinase/Peptide Mixture (zero peptide control) versus the 0% Inhibition Control. The expected value for a non-fluorescence compound should be 0%. Any value >20% is flagged.

As graphing software XLfit from IDBS is used. The dose response curve is curve fit to model number 205 (sigmoidal dose-response model). If the bottom of the curve does not fit between −20% & 20% inhibition, it is set to 0% inhibition. If the top of the curve does not fit between 70% and 130% inhibition, it is set to 100% inhibition.

Analysis of Phosphorylation of ERK in SK-MEL-28 Cells:

Fast Actived Cell-Based ELISA (FACE) SK-MEL-28 p-ERK:

Cell Culture:

SK-MEL28 cells (human melanoma) are grown in T75 flascs using MEM medium supplemented with 10% fetal calf serum, 2% Na bicarbonate, 1% Na pyruvate solution, 1% NEAA 100× and 2 mM L-Glutamine. Cultures are incubated at 37° C. and 5% CO2 in a humidified atmosphere, with medium change or subcultivation 2 times a week Assay Conditions:

7,500 cells per well/90 µl medium are plated in 96 well plates (Flat bottom, Costar #3598). At the next day compounds (Stock: 10 mM in 100% DMSO) are diluted in medium (stock solution) or serially diluted in medium plus 10% DMSO (all other dilution steps). 10 µl of diluted compound is added per well, the final concentration of DMSO is 1%. The concentration of the test compounds covers usually the range between 10 micromolar and 2.4 nanomolar minimum. Cells are incubated at 37° C. and 5% CO2 in a humidified atmosphere for 2 hours.

The supernatant is removed. Cells are fixed with 150 µl 4% formaldehyde in PBS for 20 minutes at room temperature.

The cell layer is washed 5 times with 200 µl 0.1% Triton X-100 in PBS for 5 minutes each, followed by a 90 minutes incubation with blocking buffer (5% non-fat dry milk in TBS-T). Blocking buffer is replaced by 50 µl/well of the 1st antibody [monoclonal anti-MAP Kinase diphosphorylated Erk-1&2 (Sigma, #M8159); 1:500 Verd.] and incubated over night at 4° C. The cell layer is washed 5 times with 200 µl 0.1% Triton X-100 in PBS for 5 minutes each. The cell layer is incubated with 50 µl/well of the second antibody [polyclonal rabbit-anti-Mouse HRPO coupled, (Dako, #P0161); 1:1000 dilution in blocking buffer] for 1 hour. The cell layer is washed 5 times with 200 µl 0.1% Tween20 in PBS for 5 minutes each. Peroxidase staining is performed by adding 100 µl/well of the staining solution (TMB Peroxidase Substrate Solution; Bender MedSystems #BMS406), for 5-30 minutes in the dark. The reaction is stopped by adding 100 µl/well of 1M phosphoric acid.

The stain is measured at 450 nm with a Multilabel Reader (Wallac Victor 2).

Data are fitted by iterative calculation using a sigmoidal curve analysis program (Prism version 3.0, Graph PAD) with variable hill slope (FIFTY version 2).

In vivo Efficacy

The in vivo efficacy of a dual Aurora kinase/MEK inhibitor according to this invention is assessed in standard human tumor models displaying various oncogenome signatures in nude mice: For example, xenografts derived from HCT116 (K-RAS$^{G13G/D}$ and PIK3CA$^{H1047H/R}$ mutant), and Colo205 (B-RAF$^{V600E}$ mutant) colon carcinomas, the NCI-H460 (K-RAS$^{Q61H}$ and PIK3CA$^{E545K/E}$ mutant) and Calu-6 (K-RAS$^{Q61K}$ and TP53$^{R196*}$ mutant) non-small-cell lung carcinoma, the BxPC-3 (TP53$^{Y220C}$ mutant) pancreatic carcinoma or the melanoma A-375 (B-RAF$^{V600E}$ mutant) cell lines are established models for the preclinical evaluation of oncology compounds. Tumor cells are injected subcutaneously (s.c.) into the right flank of nude mice. In addition, the efficacy of a dual MEK/Aurora B kinase inhibitor according to this invention is assessed in a nude mouse xenograft model of human colon carcinoma CxB1 with MDR1 overexpression (CxB1 tumor transplants also display K-RAS$^{G13D}$ and TP53$^{R175H\ and\ P72R}$ mutations). Mice bearing established tumors with an average volume of 50-100 mm$^3$ are randomized into treatment and control groups. Treatment is typically initiated when the tumors have reached a median volume of about 50 mm$^3$ and continued for 3 to 6 weeks. The maximum tolerated dose (MTD) is determined in tolerability tests in tumor-free nude mice before the xenograft experiment. Preferably, the dual Aurora kinase/MEK inhibitor according to this invention is administered orally (p.o.).

Efficacious treatment with the respective compound is characterised by growth delay upon treatment when used at its respective MTD. Preferably, prolonged treatment induces tumor regressions in the treated animals. Pharmacodynamic inhibition of MEK can be monitored in vivo by determining the phosphorylation state of ERK/MAPK, a direct substrate of MEK. Immunohistochemical analyses confirms target inhibition displaying a significant reduction (>50%) in pERK tumor levels in treated animals compared to vehicle-treated controls. Pharmacodynamic inhibition of Aurora B can be monitored in vivo by determining the phosphorylation state of histone H3, a substrate of Aurora B. Immunohistochemical analyses confirms target inhibition displaying a significant reduction (>50%) in phosphorylated histone H3 tumor levels in treated animals compared to vehicle-treated controls.

For example, in HCT-116 colon carcinoma treated by an exemplary dual Aurora kinase/MEK inhibitor of this invention administered at the maximum tolerated dose, phosphorylation of histone H3 by Aurora B is reduced by at least 50% compared to control tumors.

Similarly, in A-375 melanoma xenografts, phosphorylation of the MEK substrate ERK is reduced by at least 50% (or even more) in treated tumors compared to controls.

Examples of Pharmaceutical Formulations:

The following examples of formulations serve to illustrate the present invention more fully without restricting it to the contents of these examples. The term "active substance" denotes one or more compounds according to the invention, particularly denotes a dual Aurora kinase/MEK inhibitor of formula (1) according to this invention, or a combination thereof with another anti-cancer agent.

| A) | |
|---|---|
| Tablets | per tablet |
| active substance | 100 mg |
| lactose | 140 mg |
| corn starch | 240 mg |
| polyvinylpyrrolidone | 15 mg |
| magnesium stearate | 5 mg |
| | 500 mg |

The finely ground active substance, lactose and some of the corn starch are mixed together. The mixture is screened, then moistened with a solution of polyvinylpyrrolidone in water, kneaded, wet-granulated and dried. The granules, the remaining corn starch and the magnesium stearate are screened and mixed together. The mixture is compressed to produce tablets of suitable shape and size.

| B) | |
|---|---|
| Tablets | per tablet |
| active substance | 80 mg |
| lactose | 55 mg |
| corn starch | 190 mg |
| microcrystalline cellulose | 35 mg |
| polyvinylpyrrolidone | 15 mg |
| sodium-carboxymethyl starch | 23 mg |
| magnesium stearate | 2 mg |
| | 400 mg |

The finely ground active substance, some of the corn starch, lactose, microcrystalline cellulose and polyvinylpyrrolidone are mixed together, the mixture is screened and worked with the remaining corn starch and water to form a granulate which is dried and screened. The sodiumcarboxymethyl starch and the magnesium stearate are added and mixed in and the mixture is compressed to form tablets of a suitable size.

| C) Ampoule solution | |
|---|---|
| active substance | 50 mg |
| sodium chloride | 50 mg |
| water for inj. | 5 mL |

The active substance is dissolved in water at its own pH or optionally at pH 5.5 to 6.5 and sodium chloride is added to make it isotonic. The solution obtained is filtered free from pyrogens and the filtrate is transferred under aseptic conditions into ampoules which are then sterilised and sealed by fusion. The ampoules contain 5 mg, 25 mg and 50 mg of active substance.

Synthesis of 3-[3-[[4-(dimethyloxidoaminomethyl)anilino]-phenylmethylidene]-2-oxo-1H-indol-6-yl]-N-ethylprop-2-ynamide

Synthesis of 3-[3-[[4-(methylaminomethyl)anilino]-phenylmethylidene]-2-oxo-1H-indol-6-yl]-N-ethylprop-2-ynamide

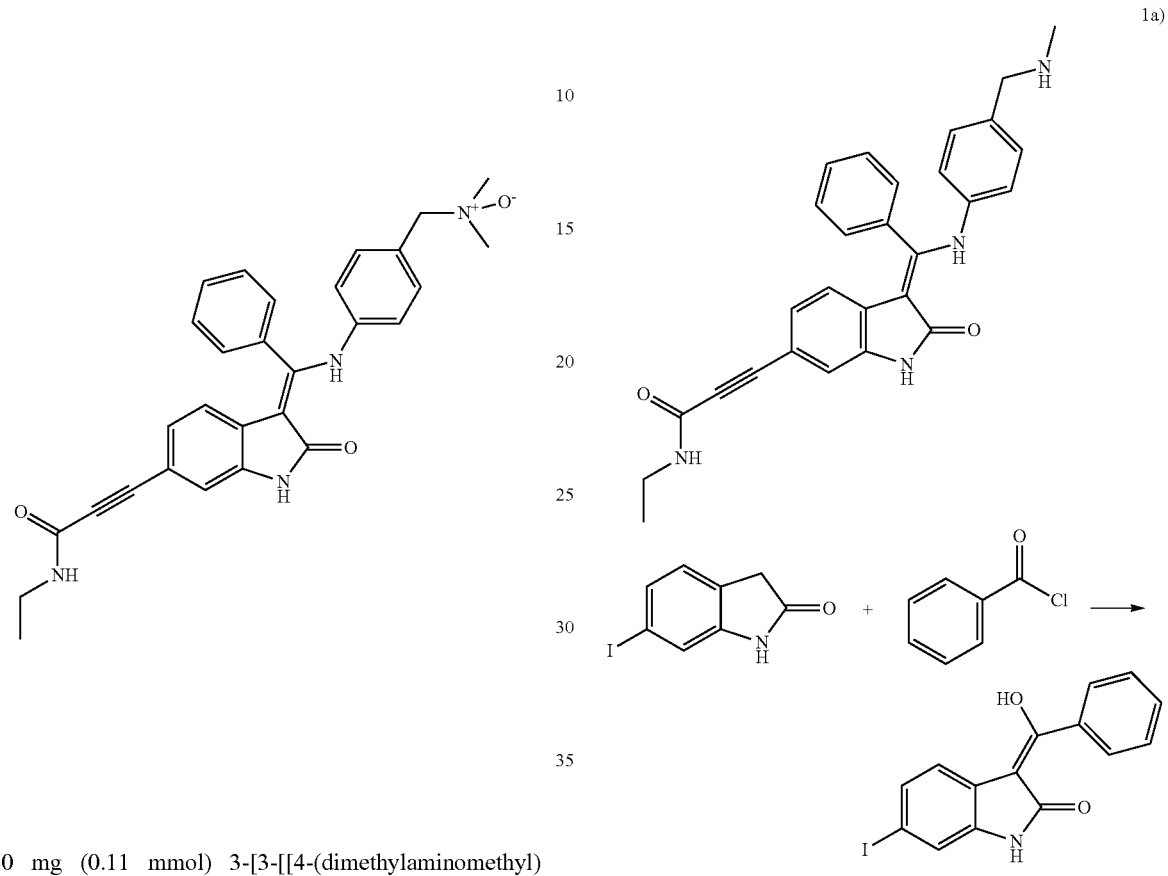

50 mg (0.11 mmol) 3-[3-[[4-(dimethylaminomethyl)anilino]-phenylmethylidene]-2-oxo-1H-indol-6-yl]-N-ethylprop-2-ynamide (cf. WO 2010/012747) are dissolved in 10.0 mL methanol and 33 µL (0.32 mmol) 30% hydrogen peroxide is added at 0° C. After 15 h stirring at 45° C. the solvent is removed. The residue is taken with dimethylsulfoxide and purified by preprative HPLC (Method B) (calculated [M−H]⁻: 479.3).

$C_{29}H_{28}N_4O_3$ (480.56)

[M+H]⁺: 481

Method B:

Equipment Agilent 1100 series (degasser; binary pump, injector, column oven) und 1200 series (DAD detector)

Column WatersXTerraPrepMSC18, 19×100 mm, 5 µ

Method Solvent A: Water (10 mM $NH_4HCO_3$, 38 mM $NH_3$) und Solvent B: Acetonitrile Flow=30 mL/min Wave length=230 nm

| time table = | 0.00 min | A 75%, B 25% |
| --- | --- | --- |
| | 6.00 min | A 30%, B 70% |
| | 6.50 min | A 5%, B 95% |
| | 7.50 min | A 5%, B 95% |

0.88 g (7.23 mmol) 4-N,N-dimethylaminopyridine and 44.6 mL (101.2 mmol) triethylamine are added successively to a suspension of 25.00 g (96.51 mmol) 6-iodo-1,3-dihydro-indol-2-one in 125.0 mL N,N-dimethylformamide. 27.81 g (197.8 mmol) benzoylchloride is added slowly at −10° C. to the reaction mixture and stirred for 2 h at −10° C. After complete conversion (HPLC, Method A) 48.0 mL 10 M sodium hydroxide solution is added and stirred 1 h at room temperature. Then 350 mL water, 150 mL toluene and 80 mL conc. hydrochloric acid are successively added. The resulting precipitate is filtered, washed with water and toluene and dried at 50° C. in vacuo.

$C_{15}H_{10}INO_2$ (363.15)

[M+H]⁺: 364

1b)

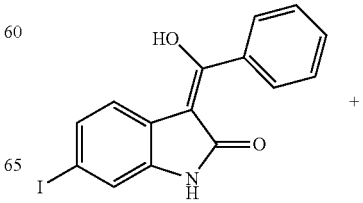

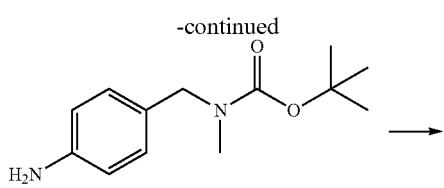

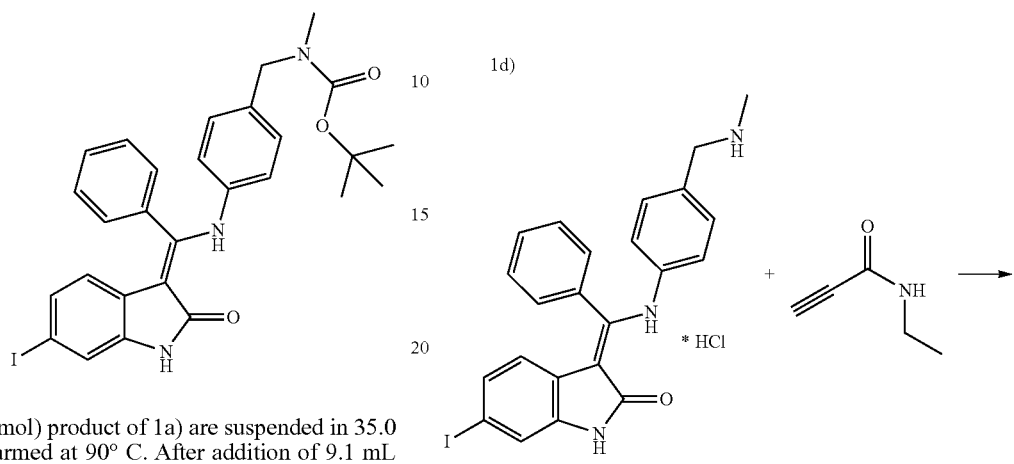

7.50 g (20.65 mmol) product of 1a) are suspended in 35.0 mL toluene are warmed at 90° C. After addition of 9.1 mL (61.96 mmol) trimethylsilylimidazole the reaction mixture is stirred for further 15 minutes at 90° C. Then 5.86 g (24.78 mmol) (4-amino-benzyl)-methyl-carbamic acid-tert-butylester (cf. WO 2008/022945) are added and 20 h stirred under reflux. After complete conversion (HPLC, Method A), the reaction mixture is cooled and 40.0 mL methanol is added. The resulting precipitate is filtered, washed with methanol and dried at 50° C. in vacuo.

$C_{28}H_{28}IN_3O_3$ (581.45)

$[M+H]^+$: 582

1c)

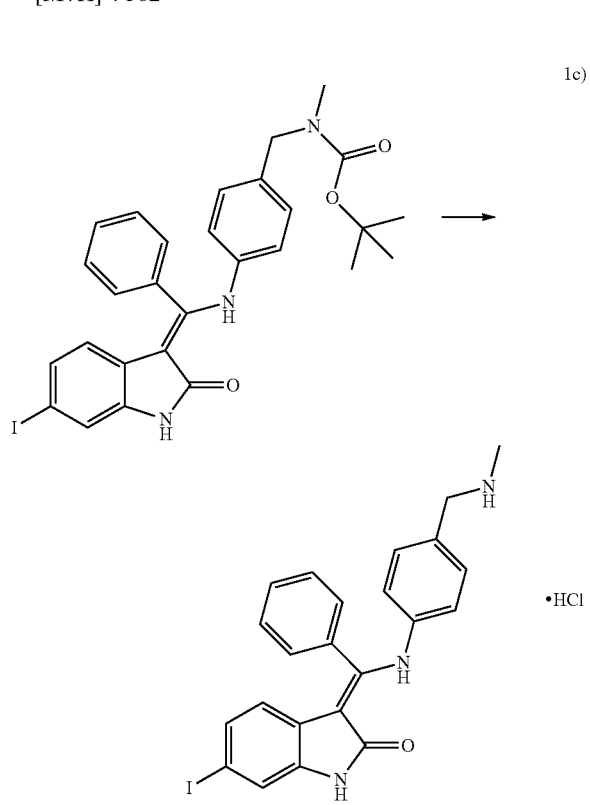

A solution of 9.00 g (15.48 mmol) product of 1b) in 135 mL ethanolic hydrochloric acid (11 mol/L) are stirred under reflux for 45 min. After complete conversion (HPLC, Method A) the reaction mixture is cooled to room temperture. The resulting precipitate is filtered, washed with Ethanol and dried at 50° C. in vacuo.

$C_{23}H_{20}IN_3O$*HCl (481.34/517.79)

$[M+Na]^+$: 504

1d)

A suspension of 5.00 g (9.66 mmol) product of 1c), 0.34 g (0.48 mmol) bis(triphenylphosphine)-palladiumdichloride and 0.24 g (1.26 mmol) cupper(I)iodide in 20.0 mL N-methylpyrrolidone is successively treated with 8.3 mL (48.0 mmol) diisopropylethylamine and 1.88 g (19.31 mmol) propiolic acid ethylamide and stirred for 20 min at 50° C. After complete conversion (HPLC) 80 ml water is added to the reaction mixture. The resulting precipitate is filtered, washed with water and chromatographically purified on silica gel ($CH_2Cl_2/CH_3OH/NH_3$ 90:10:1).

$C_{28}H_{26}N_4O_2$ (450.53)

$[M+H]^+$: 451

Method A:

Equipment Agilent 1100 series (degasser; binary pump, injector, column oven) and 1200 series (DAD)

Column Phenomenex Synergi 4u MAX-RP 80A, 75×4.6 mm

Method Solvent A: Water (0.2% ig Potassiumdihydrogenphosphate, adjusted with 5% iger phosphoric acid to pH=3) and Solvent B: Acetonitrile Flow=1.5 mL/min Wave lengthh=230 nm

| time table = | 0.00 min | A 80%, B 20% |
| --- | --- | --- |
| | 4.00 min | A 20%, B 80% |
| | 7.00 min | A 20%, B 80% |

Experimental Procedure of Proliferation Assay:

A375 and Calu6 cells are grown in RPMI1640, 10% FBS, in a humidified atmosphere of 5% $CO_2$ at 37° C. Cells are seeded into flat bottom 96 well microtiter plates and incubated in a humidified atmosphere of 5% $CO_2$ at 37° C. for 24 hours. Compounds are added, at the same time, a "time zero" untreated cell plate is stained and measured after 1 h. Compounds are serially diluted 5-fold from the highest test concentration (10 μM) and assayed over 8 concentrations in duplicates. The concentration of the solvent DMSO in the final culture is 0.1%. After a 72 hour incubation period, cells are stained with fluorescent nuclear dye to allow visualization of nuclei (CyQuant Direct Cell Proliferation Assay, Invitrogen Cat. No. C35012). Total fluorescence intensity of each well is measured using an Envision platform with excitation at 480 nm, emission detection at 535 nm. The assay signal correlates to the number of nuclei and thus, by definition, to the number of cells in the culture well ("cell count").

The cell proliferation assay output for control cells after 72 hours of incubation, corresponding to 100% cell proliferation, is taken as the reference cell count for all subsequent calculations. Relative cell proliferation in compound-treated cultures (signal percent of control, "POC") is calculated according to the following formula:

$$POC_{(t=72\ h)} = 100 * \text{fluorescence}_{(compound\ wells)}/\text{fluorescence}_{(control\ wells)}$$

In addition, for each compound-treated culture, the cell count after incubation for 72 hours ($POC_{(t=72h)}$) is related to the cell count at the start of treatment ($POC_{(t=0\ h)}$):

$$POC_{(t=0\ h)} = 100 * \text{fluorescence at } t=0_{(control\ wells)}/\text{fluorescence at } t=72\ h_{(control\ wells)}$$

The concentration-response curves were calculated using the dose-response package (drc versio 2.0-1 http://cran.rproject.org/web/packages/drc/index.html) from R (version 2.10.1 http://www.r-project.org/). The four-parameter log-logistic function (LL.4) was used without any upper or lower limitation. $GI_{50}$ values were defined as the concentration at which 50% growth inhibition is reached (halfway between the $POC_{(t=0\ h)}$ value and the upper plateau).

Relative cell growth inhibition (CGI %) in compound-treated cultures is calculated according to the following formula:

$$\% \ CGI^{72h} = \begin{cases} S_t^{72h} \geq S_c^0: & \left[1 - \frac{S_t^{72h} - S_c^{0h}}{S_c^{72h} - S_c^{0h}}\right] \times 100\% \\ S_t^{72} < S_c^0: & \left[1 - \frac{S_t^{72h} - S_c^{0h}}{S_c^{0h}}\right] \times 100\% \end{cases}$$

For example, the compounds 6, 26 and 27 of group A indicated herein have $GI_{50}$ values for antiprolifertive effect on A375 cells of 2.7, 3.37 and 17.3 nM, respectively. For further example, the compounds 6, 26 and 27 of group A indicated herein have $GI_{50}$ values for antiprolifertive effect on Calu6 cells of 7.66, 7.82 and 11.27 nM, respectively.

Western Blot Analysis of Phosphorylated ERK, MEK and HistoneH3 Levels

A375 and Calu6 cells were plated in 10 cm dishes in RPMI medium containing 10% fetal bovine serum and after overnight incubation they are treated with 1000, 100, 30, 10 nM of the compounds. 24 hours later the cells were lysed on ice with MSD/Tris Lysisbuffer (Mesoscale #R60TX2) and inhibitors (10 mM NaF, complete Mini-Protease inhibitor, Phosphatase Inhibitor II Sigma #P5726, Phosphatase Inhibitor III Sigma #P0044) and the cell lysate frozen after the protein concentration is determined by Bradford assay (BioRad Protein Assay Dye Reagent Concentration #500-0006). Total protein (20 μg) was separated on a 4-12% SDS PAGE gel (BioRad) and analyzed by immunoblotting. Membranes were blocked in 5% nonfat milk in 1×TBS/0.1% Tween 20 and then probed overnight either with a rabbit anti-beta actin (control) antibody, or a rabbit phospho-p44/42 MAPK (Erk1/2)(Thr202/Tyr204) antibody (Cell Signaling #4376), or a mouse anti-p44/42 MAPK (Erk1/2)(3A7) antibody (Cell Signaling #9107), or rabbit anti phospho H3(Ser10) antibody (Millipore #06-570), or a mouse anti Histone H3 (96C10), or a rabbit anti phospho-MEK1/2(Ser217/221) (Cell Signaling #9121), or a mouse anti MEK (BD Transduction Lab #610121). After washing and incubation with an anti-rabbit or anti-mouse IgG HRPO-conjugated secondary antibody (Amersham), the immunoblotted proteins were visualized using the ECL Western blotting detection reagent (Amersham GEH # RPN2106) according to the manufacturer's instructions.

The invention claimed is:

1. 3-[3-[[4-(dimethyloxidoaminomethy)anilino]-phenylmethylidene]-2-oxo-1H-indol-6-yl]-N-ethylprop-2-ynamide

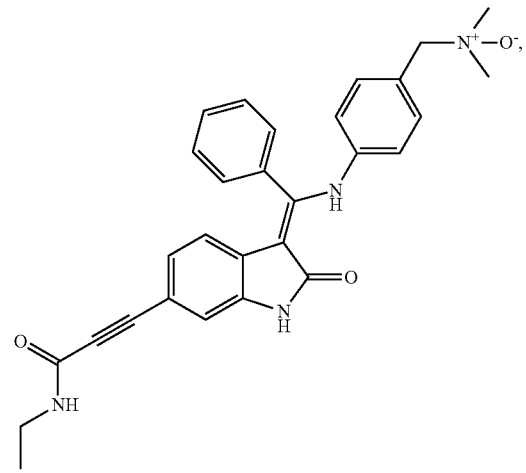

or a pharmaceutically acceptable salt thereof.

2. A pharmaceutical composition comprising the compound according to claim 1, optionally together with one or more inert carriers, diluents and/or excipients.

3. A method for treating melanoma, colorectal cancer (CRC), pancreatic cancer (PAC) or non-small cell lung cancer (NSCLC) which method comprises administering to a host suffering from the same a therapeutically effective amount of 3-[3-[[4-(dimethyloxidoaminomethyl)anilino]-phenylmethylidene]-2-oxo-1H-indol-6-yl]-N-ethylprop-2-ynamide

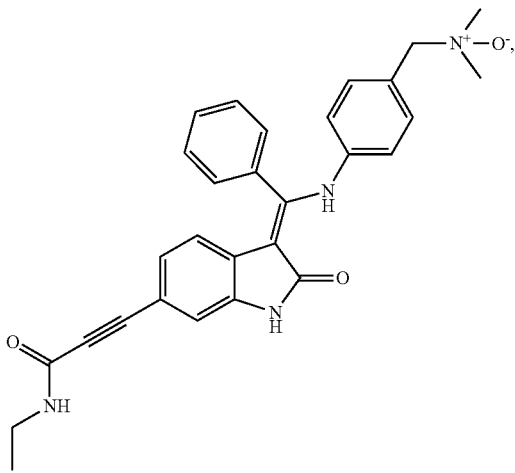

or a pharmaceutically acceptable salt thereof.

4. The method of claim 3 wherein the condition to be treated is:
colorectal cancer (CRC) harboring a KRAS mutation,
colorectal cancer (CRC) harboring wildtype KRAS,
pancreatic cancer (PAC) harboring a KRAS mutation,
pancreatic cancer (PAC) harboring wildtype KRAS,
melanoma harboring a BRAF mutation,
melanoma harboring wildtype BRAF,
melanoma harboring a NRAS mutation, and/or
non-small-cell lung cancer (NSCLC) harboring a KRAS mutation.

5. The method according to claim 4,
wherein the KRAS mutation is in codon 12, 13 or 61 of KRAS, such as e.g. selected from Gly12Asp, Gly12Val, Gly13Asp, Gly12Cys, Gly12Ser, Gly12Ala and Gly12Arg, or selected from 12D, 12V, 12C, 12A, 12S, 12R, 12F, 13D, 13C, 13R, 13S, 13A, 13V, 13I, 61H, 61L, 61R, 61K, 61E and 61P; and/or
wherein the BRAF mutation is in BRAF V600, such as e.g. selected from V600E, V600G, V600A, V600K, V600D and V600R, or selected from V600E, V600G, V600A, V600K, V600D, V600M and V600R; and/or
wherein the NRAS mutation is in codon 12, 13 or 61 of NRAS.

* * * * *